United States Patent
Bogenstaetter et al.

(10) Patent No.: US 7,265,135 B2
(45) Date of Patent: Sep. 4, 2007

(54) 2-OXY, 2-AMINO, AND 2-THIO-IMIDAZOLE COMPOUNDS

(75) Inventors: Michael Bogenstaetter, London (GB); Nicholas I. Carruthers, Poway, CA (US); Jill A. Jablonowski, San Diego, CA (US); Timothy W. Lovenberg, San Diego, CA (US); Kiev S. Ly, San Diego, CA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 309 days.

(21) Appl. No.: 10/757,625

(22) Filed: Jan. 14, 2004

(65) Prior Publication Data

US 2004/0147577 A1 Jul. 29, 2004

Related U.S. Application Data

(63) Continuation of application No. 10/104,283, filed on Mar. 22, 2002, now abandoned.

(60) Provisional application No. 60/279,802, filed on Mar. 29, 2001.

(51) Int. Cl.
- *C07D 401/12* (2006.01)
- *C07D 401/14* (2006.01)
- *C07D 233/84* (2006.01)
- *A61K 31/4178* (2006.01)
- *A61P 25/08* (2006.01)

(52) U.S. Cl. .............. 514/326; 548/314.7; 548/322.5; 548/323.5; 548/324.5; 548/325.1; 548/331.5; 548/332.1; 546/210; 514/397; 514/398; 514/400

(58) Field of Classification Search ............. 548/314.7, 548/322.5, 323.5, 324.5, 325.1, 331.5, 332.1; 546/210; 514/326, 397, 398, 400
See application file for complete search history.

(56) References Cited

U.S. PATENT DOCUMENTS

| | | | | |
|---|---|---|---|---|
| 3,714,179 | A | * | 1/1973 | Tweit ................... 548/315.7 |
| 3,886,160 | A | * | 5/1975 | Tweit ..................... 544/316 |
| 5,030,644 | A | * | 7/1991 | Baldwin et al. ............ 514/393 |
| 5,217,986 | A | | 6/1993 | Pomponi et al. |
| 5,352,707 | A | | 10/1994 | Pompni et al. |
| 5,869,479 | A | | 2/1999 | Kreutner et al. |
| 2005/0250948 | A1 | * | 11/2005 | Jones et al. ............. 548/331.1 |

FOREIGN PATENT DOCUMENTS

| | | |
|---|---|---|
| EP | 0 978 512 A1 | 2/2000 |
| JP | 02306237 A2 * | 12/1990 |
| WO | WO99/42458 | 8/1999 |

OTHER PUBLICATIONS

Jordaan, A.; Arndt, R. R., Journal of Heterocyclic Chemistry, 5(5), 723-5 (English) 1968.*
Garcia Gonzalez, F.; Fernandez Bolanos, J.; Fuentes Mota, J., Carbohydrate Research, 22(2), 436-40 (English) 1972.*
Renato M.E. Sabbatini,. Re: The Cyclotron and PET. In Brain & Mind an electronic magazine about Neuroscience [online], Mar. 1997 [retrived Jul. 15, 2003]. Retrived from the internet <http://www.epub.org.br/cm/n01/pet/petcyclo.htm>.*
Phillips, J.G. et al, Ann. Reports Med. Chem., 31, 1998, pp. 31-40.*
West, Anthony R., Solid State Chemistry and its Applications, Wiley, New York, 1988, pp. 358 & 365.*
Phillips, Brian T.; Claremon, David A.; Varga, Sandor L., Synthesis (9), 761-3 (English) 1990.*
Anjaneyulu, B. et al. Synthesis of 14C-Labelled 1-Methanesulphonyl-3-(1-methyl-5-nitro-1H-imidazol-2-yl)-2-imidazolidinone, (Go 10213). J. Labelled Compd. Radiopharm. (1983) 20(8):951-961.
Iemura, R. et al. Synthesis of Benzimidazole Derivatives as Potential. H1-Antihistaminic Agents. J. Heterocycl. Chem. (1987) 24:31-37.
Iwata, R. et al. Synthesis of 3-[1H-Imidazol-4-yl]propyl 4-[18F]fluorobenzyl Ether ([18 F]Fluoroproxyfan): A Potential Radioligand for Imaging Histamine H3 Receptors. J. Labelled Compd. Radiopharm. (2000) 43:873-882.
Jarosinski, M.A.; Anderson, W.K. Preparation of Noncondensed 2-Substituted 1-Methylimidazoles via Ipso Substitution Reaction on 2-Sulfinyl or 2-Sulfonyl Derivatives of 4,5-Disubstituted 1-Methylimidazoles. J. Org. Chem. (1991) 56(12):4058-4062.
Ohta, S. et al. Synthesis and Application of Imidazole Derivatives. Introduction of Carbogenic Substituents into the 5-Position of 1-Methyl-1H-imidazole. Chem. Pharm. Bull. (1992) 40(10):2681-2685.
Phillips, B.T. et al. Preparation of 5-Substituted 2-Mercapto-1-methylimidazoles. Direct Metalation of 2-Mercapto-1-methylimidazole. Synthesis (1990) :761-763.
Schnettler, R.A. et al. 4-Aroyl-1,3-dihydro-2H-imidazol-2-ones, a New Class of Cardiotonic Agents. J. Med. Chem. (1982) 25:1477-1481.
Shapiro, G.; Marzi, M. Synthesis of 2,5-Dilithio-1-methylimidazole. Tetrahedron Lett. (1993) 34(21):3401-3404.
Leurs, R. et al; "Therapeutic potential of histamine H3 recepto agnoists and antagonitsts" Trends n Pharmacological sciences, Elsevier Trends Journal, Cambridge, BG, vol. 19, No. 5, May 1, 1998; pp. 177-184, XP004121095.

(Continued)

Primary Examiner—Kahsay Habte

(57) ABSTRACT

The invention relates to novel 2-Oxy, 2-Amino, and 2-Thio-imidazole compounds of formula (I):

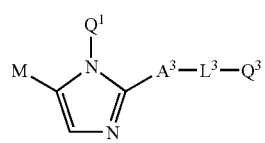

wherein all variables are as herein defined, pharmaceutical compositions containing the compounds and methods of using them in the treatment of neurological disorders and other disorders and conditions mediated by the histamine $H_3$ receptor.

14 Claims, No Drawings

OTHER PUBLICATIONS

Tozer, M.J., et al.; "From Histamine to imidazolylalkyl-sulfonamides: the design of a novel series of histamine H3 receptor antagonists"; Bioorganic & Medicinal CHemistry Letters, OXFORD, GB, vol. 9, No. 13, Jul. 5, 1999, pp. 1825-1830. XP004168846.

Gonzalez, F. Garcia et al.: "Synthesis of 3-aryl(alkyl)-4-(D-*arabino*-tetrahydroxybutyl)imidazolin—2-thiones"; J. Carbohydrate Research. 22(1972), 436-40.

Jordaan, A. et al.: "The Synthesis of 1-Methyl-5-(α-indolyl)imidzaole"; J. of Heterocyclic Chemistry, 5(5), 723-5 (1968).

Phillips, J.G. et al.: Chapter 4. Recent Advance in Histamine $H_3$ Receptor Agents. Annual Reports in Medicinal Chem., 33, 1998, pp. 31-40.

Sabbatini, Renato M.E.: Re: The Cyclotron and PET. In Brain & Mind an electronic magazine about Neuroscience [online]. Mar. 1997. Retrieved from the Internet <http://www.epub.org.br/cm/n01/pet/petcyclo.htm>.

Arrang, J.M. et al.; "Auto-inhibiton of brain histamine release mediated by novel class (h3) of histamine receptor" Nature; Apr. 1983; 302:832-837.

Ash, A.S.F. et al; "Receptors Mediating Some Actions of Histamine"; Br. J. Pharmac. Chemother.; 1966 27:427-439.

Barnes, J.C. et al; "The selective Histamine H3 Receptor Antagonist Thioperamide Improves Cognition and Enhances Hippocampal Acetylcholine Release in vivo"; Soc. Neurosci. Abstr.; 1993 19:1813.

Bioworld Today, Mar. 2, 1999, p. 3.

Black, J.W. et al.; "Definition and Antagonism of Histamine H2-receptors"; Nature; Apr. 1972; 236:385-390.

Ding, Y. S. et al. "Synthesis of High Specific Activity (+)-and (−)6-[18F]Fluoronorepinephrine via the Nucleophilic Aromatic Substitution Reaction". J. Med. Chem. (1991) 34:767-771.

Ganellin, C.R. et al.; "Synthesis of Potent Non-Imidazole Histamine H3-Receptor Antagonists"; Arch. Pharm. Pharm. Med. Chem. (Weinheim, Ger.); 1998 331:395-404.

Garbag, M. et al; "S-[2-(4-Imidazolyl)ethyl]Isothiourea, a Highly Specific and Potent Histamine H3 Receptor Agonist"; J. Pharmacol. Exp. Ther.; 1992; 263(1):304-310.

Gilatech, Inc.; "Gilatech's first drug candidate begins phase I human clinical trials"; Gilatech Inc. Press Release; Nov. 5, 1998.

Ichinose, M. et al; "Histamine H3-receptors modulate nonadrenergic noncholinergic neural bronchoconstriction in guinea-pig in vivo"; P.J. Eur. J. Pharmacol; 1989; 174:49-55.

Imamura, M. et al.; "Unmasking of Activated Histamine H3-Receptors in Myocardial Ischemia: Their Role as Regulators of Exocytotic Norepinephrine Release 1,2"; J. Pharmacol, Exp. Ther.; 1994 271(3):1259-1266.

Jones, R.G. Studies on Imidazoles. II. The Synthesis of 5-Imidazolecarboylates from Glycine and Substituted Glycine Esters. J Am. Chem Soc. (1949) 71:644-647.

Korte, A. et al; "Characterization and Tissue Distribution of H3 Histamine Receptors in Guinea Pigs by Na-Methylhistamine"; Biochem. Biophys. Res. Commun.; May 1990; 168(3):979-986.

Krause, M. et al.; "The Histamine H3 Receptor-A Target for New Drugs"; Leurs, R.; Timmerman, H. (Eds.); Elsevier; 1998; 175-196.

Leurs, R. et al; "The medicinal chemistry and therapeutic potentials of ligands of the histamine h3 receptor" Prog. Drug. Res.; 1995; 45:107-165.

Lin, Jian-Sheng et al. "Involvement of histaminergic neurons in arousal mechanisms demonstrated with H3-receptor ligands in the cat"; Brain Res.; 1990; 523:325-330.

Linney, I.D. et al; "Design, Synthesis, and Structure-Activity Relationships of Novel Non-Imidazole Histamine H3 Receptor Antagonists"; J. Med. Chem.; 2000; 43:2362-2370.

Lovenberg, T.W. et al; "Cloning and Functional Expression of the Human Histamine H3 Receptor"; Mol. Pharmacol; 1999 55:1101-1107.

Lovenberg, T.W. et al. Cloning of Rat Histamine H3 Receptor Reveals Distinct Species Pharmacological Profiles. J. Pharmacol. Exp. Ther. (2000) 293:771-778.

Machidori, H. et al; "Zucker obese rats:defect in brain histamine control of feeding"; Brain Res.; 1992; 590:180-186.

Mcleod, R.L. et al; "Antimigraine and Sedative Activity of SCH 50971: A Novel Orally-Active Histamine H3 Receptor Agonist"; Soc. Neurosci. Abstr.; 1996; 22:2010.

Monti, J.M. et al; "Effects of selective activation or blockade of the histamine h3 receptor on sleep and wakefulness"; Eur. J. Pharmarcol.; 1991; 205:283-287.

Morisset, S. et al; "High constitutive activity of native H3 receptors regulates histamine neurons in brain"; Nature; Dec. 2000; 408:860-864.

Oda, Tamaki et al.; "Molecular Cloning and characterization of a Novel Type of Histamine Receptor Preferentially Expressed In Leukocytes"; J. Biol. Chem.; Nov. 2000; 275(47):36781-36786.

Panula, P. et al.; "Significant Changes in the Human Brain Histaminergic System in Alzheimer's Disease"Soc. Neurosci. Abstr.; 1995; 21:1977.

Phelps, M.E. "Positron Emission Tomography Provides Molecular Imaging of Biological Processes." Proc. Natl. Acad. Sci. (2000) 97:9226-9233.

Phillips, J.G.; Ali, S.M. "In the Histamine H3 Receptor-A Target for New Drugs" Leurs, R.; Timmerman, H. (Eds.) Elsevier (1998) 197-222.

Schlicker, E., et al.; "The moderate affinity of clozapine at H3 receptors is not shared by its two major metab olites and by structurally related and unrelated atypical neuroleptics"; Naunyn-Schmiedeberg's Arch. Pharmacol.; 1996 353:290-294.

Stark, H. et al.; "Developments of histamine H3-receptor antagonists"; Drugs Future; 1996; 21(5):507-520.

Tozer, M.J., et al.: "Histamine H3 receptor antagonists"; Exp. Opin. Ther. Patents; 2000 10:1045-1055.

Walczynski, K., et al.; "Non-imidazole Histamine H3 Ligands, Part 2; New 2-Substituted Benzothiazoles as Histamine H3 Antagonists"; Arch. Pharm. Pharm. Med. Chem. (Weinheim, Ger.); 1999 332:389-398.

Walczynski, K. et al.; "Non-imidazole histamine H3 ligands. Part I. Synthesis of 2-(1-piperazinyl)- and 2-(hexahydro-1H-1,4-diazepin-1-yl)benzoyhiazole derivatives as H3 antagonists with H1 blocking activities"; IL Farmaco; 1999; 54:684-694.

West, R.E. Jr: et al.; "The Profiles of Human and Primate [3H]Na-Methylhistamine Binding Differ From That of Rodents"; Eur. J. Pharmacol.; 1999; 377:233-239.

West, Robert E. et al.; "Identification of Two H3-Histamine Receptor Subtypes"; Mol. Pharmacol.; 1990 38:610-613.

Yokoyama, H. et al., "Effect of thioperamide, a histamine h3 receptor antagonist, on electrically induced convulsions in mice"; Eur. J. Pharmacol. ; 119 234:129-133.

\* cited by examiner

2-OXY, 2-AMINO, AND 2-THIO-IMIDAZOLE COMPOUNDS

This application is a continuation of U.S. Ser. No. 10/104,283 filed Mar. 22, 2002, now abandoned which claims the benefit of U.S. provisional application No. 60/279,802 filed Mar. 29, 2001.

FIELD OF THE INVENTION

The present invention relates to heterocyclic derivatives useful in methods of treating neurologic and other disorders and conditions mediated by the histamine $H_3$ receptor.

BACKGROUND OF THE INVENTION

Histamine [2-(imidazol-4-yl)ethylamine] is a transmitter substance. Histamine exerts a physiological effect via multiple distinct G-protein coupled receptors. It plays a role in immediate hypersensitivity reactions and is released from mast cells following antigen IgE antibody interaction. The actions of released histamine on the vasculature and smooth muscle system account for the symptoms of the allergic response. These actions occur at the $H_1$ receptor (Ash, A. S. F. and Schild, H. O., *Br. J. Pharmacol.*, 1966, 27, 427) and are blocked by the classical antihistamines (e.g. diphenhydramine). Histamine is also an important regulator of gastric acid secretion through its action on parietal cells. These effects of histamine are mediated via the $H_2$ receptor (Black, J. W., Duncan, W. A. M., Durant, C. J., Ganellin, C. R. and Parsons, E. M., *Nature*, 1972, 236, 385) and are blocked by $H_2$ receptor antagonists (e.g. cimetidine). The third histamine receptor —$H_3$— was first described as a presynaptic autoreceptor in the central nervous system (CNS) (Arrang, J.-M., Garbarg, M., and Schwartz, J.-C., *Nature* 1983, 302, 832) controlling the synthesis and release of histamine. Recent evidence has emerged showing that the $H_3$ receptors are also located presynaptically as heteroreceptors on serotonergic, noradrenergic, dopaminergic, cholinergic, and GABAergic (gamma-aminobutyric acid containing) neurons. These $H_3$ receptors have also recently been identified in peripheral tissues such as vascular smooth muscle. Consequently there are many potential therapeutic applications for histamine $H_3$ agonists, antagonists, and inverse agonists. (See: "*The Histamine $H_3$ Receptor-A Target for New Drugs*", Leurs, R., and Timmerman, H., (Editors), Elsevier, 1998; Morisset et al., *Nature*, 2000, 408, 860-864.) A fourth histamine receptor —$H_4$— was recently described by Oda et al., (J. Biol. Chem., 2000, 275, 36781-36786).

The potential use of histamine $H_3$ agonists in sleep/wake and arousal/vigilance disorders is suggested based on animal studies (Lin et al, *Br. Res.*, 1990, 523, 325; Monti et al *Eur. J. Pharmacol.*, 1991, 205, 283). Their use in the treatment of migraine has also been suggested (McLeod et al *Abstr. Society Neuroscience*, 1996, 22, 2010) based on their ability to inhibit neurogenic inflammation. Other applications could be a protective role in myocardial ischemia and hypertension where blockade of norepinephrine release is beneficial (Imamura et al *J. Pharmacol. Expt. Ther.*, 1994, 271, 1259). It has been suggested that histamine $H_3$ agonists may be beneficial in asthma due to their ability to reduce non-adrenergic non-cholinergic (NANC) neurotransmission in airways and to reduce microvascular leakage (Ichinose et al *Eur. J. Pharmacol.*, 1989, 174, 49).

Several indications for histamine $H_3$ antagonists and inverse agonists have similarly been proposed based on animal pharmacology experiments with known histamine $H_3$ antagonists (e.g. thioperamide). These include, dementia, Alzheimer's disease (Panula et al *Abstr. Society Neuroscience*, 1995, 21, 1977), epilepsy (Yokoyama et al *Eur. J. Pharmacol.*, 1993, 234, 129) narcolepsy, eating disorders (Machidori et al *Brain Research* 1992, 590, 180), motion sickness, vertigo, attention deficit hyperactivity disorders (ADHD), learning and memory (Barnes et al *Abstr. Society Neuroscience*, 1993, 19, 1813), schizophrenia (Schlicker et al *Naunyn-Schmiedeberg's Arch. Pharmacol.*, 1996, 353, 290-294); (also see; Stark et al *Drugs of the Future*, 1996, 21, 507 and Leurs et al *Progress in Drug Research*, 1995, 45, 107 and references cited therein). Histamine $H_3$ antagonists, alone or in combination with a histamine $H_1$ antagonist, are reported to be useful for the treatment of upper airway allergic response (U.S. Pat. Nos. 5,217,986; 5,352,707 and 5,869,479). Recently, a histamine $H_3$ antagonist (GT-2331) was identified and is being developed by Gliatech Inc. (Gliatech Inc. Press Release Nov. 5, 1998; *Bioworld Today*, Mar. 2, 1999) for the treatment of CNS disorders.

As noted, the prior art related to histamine $H_3$ ligands was comprehensively reviewed recently ("*The Histamine $H_3$ Receptor-A Target for New Drugs*", Leurs, R., and Timmerman, H., (Editors), Elsevier, 1998). Within this reference the medicinal chemistry of histamine $H_3$ agonists and antagonists was reviewed (see Krause et al and Phillips et al respectively). Thus the importance of an imidazole moiety containing only a single substitution in the 4 position was noted together with the deleterious effects of additional substitution on activity. Particularly methylation of the imidazole ring at any of the remaining unsubstituted positions was reported to strongly decrease activity.

More recently several publications have described histamine $H_3$ ligands that do not contain an imidazole moiety. For example; Ganellin et al *Arch. Pharm. (Weinheim, Ger.)* 1998, 331, 395; Walczynski et al *Arch. Pharm. (Weinheim, Ger.)* 1999, 332, 389; Walczynski et al Farmaco 1999, 684; Linney et al *J. Med. Chem.* 2000, 2362; Tozer and Kalindjian *Exp. Opin. Ther. Patents* 2000, 10, 1045-1055; U.S. Pat. No. 5,352,707; PCT Application WO99/42458, Aug. 26, 1999; and European Patent Application 0978512, Feb. 9, 2000.

We now describe a series of heterocyclic derivatives with the ability to modulate the activity of the histamine receptor, specifically the $H_3$ receptor.

SUMMARY OF THE INVENTION

The present invention provides compounds of the formula (I):

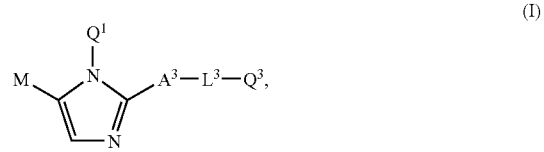

wherein:
  $Q^1$ is selected from the group consisting of $C_{1-7}$ alkyl, $C_{1-7}$ haloalkyl and $C_{2-7}$ alkenyl;
    wherein $Q^1$ may be substituted with one or more substituents selected from the group consisting of halo, cyano, hydroxy, $OR^{11}$, $C_{1-5}$ alkyl, $C_{1-5}$ haloalkyl, $C_{2-5}$ alkenyl, nitro, amino($H_2N$—), $R^{11}HN-$, $R^{11}R^{12}N-$, amido($H_2NC(O)$), $R^{11}HNC(O)$, $R^{11}R^{12}NC(O)$ and $R^{11}OC(O)$, and wherein $R^{11}$ and $R^{12}$ are independently $C_{1-5}$ alkyl, $C_{1-5}$ haloalkyl or $C_{2-5}$ alkenyl;

M is a moiety of the formula $-CH_2R^M$, $-CHOHR^M$, $-C(=O)R^M$ or $-C(=N-OH)R^M$, wherein, $R^M$ is selected from the group consisting of $C_{1-7}$ alkyl, $R^{M1}HN-$, $R^{M1}R^{M2}N-$, cycloalkyl, aryl, biaryl and heterocyclyl, wherein $R^M$ may be substituted with one or more substituents independently selected from the group consisting of halo, cyano, hydroxy, $OR^{M1}$, $C_{1-5}$ alkyl, $C_{1-5}$ haloalkyl, $C_{2-5}$ alkenyl, nitro, amino ($H_2N-$), $R^{M1}HN-$, $R^{M1}R^{M2}N-$, amido($H_2NC(O)$), $R^{M1}HNC(O)$ and $R^{M1}R^{M2}NC(O)$, and wherein $R^{M1}$ and $R^{M2}$ are independently $C_{1-5}$ alkyl, $C_{1-5}$ haloalkyl or $C_{2-5}$ alkenyl;

or M is hydrogen;

$A^3$ is NH, $NR^3$, sulfur, sulfoxide, sulfone or oxygen, wherein $R^3$ is $C_{1-5}$ alkyl;

$L^3$ is $C_{1-7}$ alkyl or $C_{2-7}$ alkenyl;

wherein $L^3$ may be substituted with one or more substituents selected from the group consisting of halo, hydroxy, methoxy and amino ($H_2N-$);

or $L^3$ is absent; and $Q^3$ is selected from the group consisting of $C_{1-7}$ alkyl, $C_{1-7}$ haloalkyl, $C_{2-7}$ alkenyl, $C_{3-7}$ cycloalkyl, $C_{5-7}$ cycloalkenyl, aryl, 4-7 membered heterocyclyl, ($C_{3-7}$cycloalkyl)-(4-7 membered heterocyclyl, 4-7 membered heterocyclyl)-$C_{3-7}$ cycloalkyl, bi-(4-7 membered heterocyclyl), $R^{31}HN-$, $R^{31}R^{32}N-$, azinoyl($R^{31}HN^+$($O^-$) or $R^{31}R^{32}N^+(O^-)$), $C_{3-7}$ cycloalkylamino, 4-7 membered heterocyclylamino, aryl $C_{1-6}$ alkylamino, $C_{3-7}$ cycloalkylsulfanyl, 4-7 membered heterocyclylsulfanyl and 4-7 membered heterocyclyloxy;

wherein $Q^3$ may be substituted with one or more substituents selected from the group consisting of halo, cyano, hydroxy, $OR^{31}$, $C_{1-5}$ alkyl, $C_{1-5}$ haloalkyl, $C_{2-5}$ alkenyl, nitro, amino($H_2N-$), $R^{31}HN-$, $R^{31}R^{32}N-$, amido($H_2NC(O)$), $R^{31}HNC(O)$, $R^{31}R^{32}NC(O)$, $R^{31}OC(O)$, $C_{3-7}$ cycloalkyl, monocyclic 4-7 membered heterocyclyl and monocyclic 4-7 membered heterocyclyl $C_{1-6}$ alkyl, and wherein $R^{31}$ and $R^{32}$ are independently $C_{1-5}$ alkyl, $C_{1-5}$ haloalkyl or $C_{2-5}$ alkenyl;

or $A^3$ and $L^3$ are absent and $Q^3$ is sulfanyl;

or a pharmaceutically acceptable ester, ether, N-oxide, amide, salt, hydrate or isotopically labeled form thereof.

The disclosed compounds, alone or in combination with a histamine $H_1$ receptor antagonist or a histamine $H_2$ receptor antagonist, are useful for treating or preventing neurologic disorders including sleep/wake and arousal/vigilance disorders (e.g. insomnia and jet lag), attention deficit hyperactivity disorders (ADHD), learning and memory disorders, cognitive dysfunction, migraine, neurogenic inflammation, dementia, mild cognitive impairment (pre-dementia), Alzheimer's disease, epilepsy, narcolepsy, eating disorders, obesity, motion sickness, vertigo, schizophrenia, substance abuse, bipolar disorders, manic disorders and depression, as well as other histamine $H_3$ receptor mediated disorders such as upper airway allergic response, asthma and allergic rhinitis in a subject in need thereof.

The present invention also provides process intermediates useful in preparing compounds of Formula I. A preferred embodiment of the present invention is an intermediate compound of the formula (II):

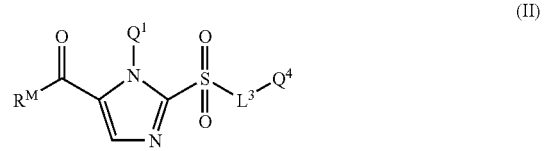

wherein:

$Q^1$ is selected from the group consisting of $C_{1-7}$ alkyl, $C_{1-7}$ haloalkyl and $C_{2-7}$ alkenyl;

wherein $Q^1$ may be substituted with one or more substituents selected from the group consisting of halo, cyano, hydroxy, $OR^{11}$, $C_{1-5}$ alkyl, $C_{1-5}$ haloalkyl, $C_{2-5}$ alkenyl, nitro, amino($H_2N-$), $R^{11}HN-$, $R^{11}R^{12}N-$, amido($H_2NC(O)$), $R^{11}HNC(O)$, $R^{11}R^{12}NC(O)$ and $R^{11}OC(O)$, and wherein $R^{11}$ and $R^{12}$ are independently $C_{1-5}$ alkyl, $C_{1-5}$ haloalkyl or $C_{2-5}$ alkenyl;

$R^M$ is selected from the group consisting of methyl, $R^{M1}HN-$, $R^{M1}R^{M2}N-$, $C_{5-7}$ cycloalkyl (e.g., cyclopentyl or cyclohetyl), aryl, biaryl (e.g., haphthyl, or (4-phenyl)phenyl and 4-7 membered heterocyclyl with between 0 and 2 heteroatoms, wherein $R^M$ may be substituted with one or more substituents independently selected from the group consisting of halo, cyano, hydroxy, $OR^{M1}$, $C_{1-5}$ alkyl, $C_{1-5}$ haloalkyl, $C_{2-5}$ alkenyl, nitro, amino ($H_2N-$), $R^{M1}HN-$, $R^{M1}R^{M2}N-$, amido($H_2NC(O)$), $R^{M1}HNC(O)$ and $R^{M1}R^{M2}NC(O)$, and wherein $R^{M1}$ and $R^{M2}$ are independently $C_{1-5}$ alkyl, $C_{1-5}$ haloalkyl or $C_{2-5}$ alkenyl;

$L^3$ is $C_{1-7}$ alkyl or $C_{2-7}$ alkenyl;

wherein $L^3$ may be substituted with one or more substituents selected from the group consisting of halo, hydroxy, methoxy and amino ($H_2N-$);

or $L^3$ is absent; and $Q^4$ is hydrogen;

or a derivative thereof that bears one or more protecting groups.

DETAILED DESCRIPTION OF THE INVENTION

The present invention provides compounds of the formula (I):

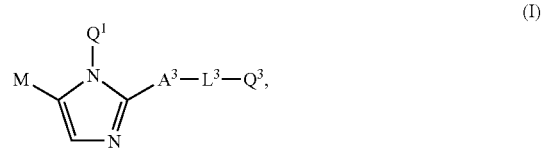

and the formula (II):

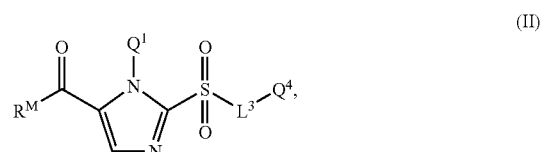

described in the Summary section above. The invention encompasses the described compounds or pharmaceutically acceptable esters, ethers, N-oxides, amides, salts, hydrates or isotopically labeled forms thereof.

A preferred embodiment of the present invention is a compound of Formula I wherein $Q^1$ is unsubstituted or substituted $C_{1-7}$ alkyl, more preferably unsubstituted or substituted $C_{1-5}$ alkyl, and most preferably unsubstituted $C_{1-3}$ alkyl. Preferred substituents are those having a basic amine.

A preferred embodiment of the present invention is a compound of Formula I wherein $Q^1$ is methyl.

Another preferred embodiment of the present invention is a compound of Formula I wherein M is a moiety of the formula —$CH_2R^M$, —$CHOHR^M$, —$C(=O)R^M$ or —$C(=N-OH)R^M$, and more preferably —$CHOHR^M$, —$C(=O)R^M$ or —$C(=N-OH)R^M$.

Another preferred embodiment of the present invention is a compound of Formula I wherein $R^M$ is unsubstituted or substituted $C_{3-7}$ cycloalkyl, aryl or 4-7 membered heterocyclyl.

Another preferred embodiment of the present invention is a compound of Formula I wherein $R^M$ is aryl, and more preferably phenyl, unsubstituted or substituted with halo, cyano, hydroxy, methoxy, $C_{1-3}$ alkyl, perhalomethyl, nitro or amino, and preferably substituted with F, Cl, Br, cyano, methoxy, $C_{1-3}$ alkyl, hydroxy, $CF_3$ or nitro.

Another preferred embodiment of the present invention is a compound of Formula I wherein $A^3$ is oxygen, sulfur or NH, and more preferably oxygen or sulfur, and most preferably oxygen.

Another preferred embodiment of the present invention is a compound of Formula I wherein $L^3$ is unsubstituted or substituted $C_{1-5}$ alkyl or $C_{2-5}$ alkenyl.

Another preferred embodiment of the present invention is a compound of Formula I wherein: $L^3$ is selected from (a) $C_{1-3}$ alkyl, which may be unsubstituted or substituted, and independently may be unbranched or branched, and (b) $C_{4-5}$ alkyl, which is branched or substituted, or both. Examples of preferred $L^3$ include methyl, ethyl, propyl, 1-methylethyl (isopropyl), 1-methylpropyl, 2-methylpropyl, 1-methylbutyl, 2-methylbutyl, 3-methylbutyl and 2-ethylpropyl.

Another preferred embodiment of the present invention is a compound of Formula I wherein $L^3$ is absent.

Another preferred embodiment of the present invention is a compound of Formula I wherein $Q^3$ is $R^{31}HN$— or $R^{31}R^{32}N$—, or an unsubstituted or substituted nitrogen-containing 5-6 membered heterocyclyl, $C_{3-6}$ cycloalkyl-5-6 membered heterocyclyl, 5-6 membered heterocyclyl —$C_{3-6}$ cycloalkyl or bi-heterocyclyl, and more preferably $R^{31}R^{32}N$— or an unsubstituted or substituted nitrogen-containing 5-6 membered heterocyclyl.

Another preferred embodiment of the present invention is a compound of Formula I wherein: $Q^1$ is methyl; M is a moiety of the formula —$CH_2R^M$, —$CHOHR^M$, —$C(=O)R^M$ or —$C(=N-OH)R^M$; $R^M$ is phenyl (or pyridinyl, or both) unsubstituted or substituted with F, Cl, Br, cyano, methoxy, $C_{1-3}$ alkyl, $CF_3$ or nitro; $A^3$ is oxygen or sulfur; $L^3$ is selected from (a) $C_{1-3}$ alkyl, which may be unsubstituted or substituted, and independently may be unbranched or branched, and (b) $C_{4-5}$ alkyl, which is branched or substituted, or both; and $Q^3$ is $R^{31}R^{32}N$—.

Another preferred embodiment of the present invention is a compound of Formula I wherein: $Q^1$ is methyl; M is a moiety of the formula —$CH_2R^M$, —$CHOHR^M$ or —$C(=O)R^M$; $R^M$ is phenyl unsubstituted or substituted with F, Cl, Br, cyano, methoxy, $C_{1-3}$ alkyl, $CF_3$ or nitro; $A^3$ is oxygen or sulfur; $L^3$ is unsubstituted or substituted $C_{1-5}$ alkyl or $C_{2-5}$ alkenyl, or $L^3$ is absent; and $Q^3$ is an unsubstituted or substituted nitrogen-containing 5-6 membered heterocyclyl (e.g., piperidino, piperazino, or N-substituted 4-piperidinyl).

Another preferred embodiment of the present invention is a compound of formula I wherein:
$Q^1$ is $C_{1-3}$ alkyl
  wherein $Q^1$ may be substituted with one substituent selected from the group consisting of amino, $R^{11}HN$—, $R^{11}R^{12}N$—, amido, $R^{11}HNC(O)$, $R^{11}R^{12}NC(O)$ and $R^{11}OC(O)$, and
  wherein $R^{11}$ and $R^{12}$ are independently $C_{1-5}$ alkyl, $C_{1-5}$ haloalkyl or $C_{2-5}$ alkenyl;
M is a moiety of the formula —$CH_2R^M$, —$CHOHR^M$, or —$C(=O)R^M$,
  wherein, $R^M$ is selected from the group consisting of $C_{1-3}$ alkyl, $R^{M1}HN$—, $C_{1-3}R^{M1}R^2N$—, $C_{5-7}$ cycloalkyl, aryl, biaryl and 4-7 membered heterocyclyl containing between 1 and 2 heteroatoms,
  wherein $R^M$ may be substituted with one or more substituents independently selected from the group consisting of halo, cyano, hydroxy, $OR^{M1}$, $C_{1-5}$ alkyl, nitro, and amino; and
$A^3$ is sulfur or oxygen
$L^3$ is $C_{1-7}$ alkyl or $C_{2-7}$ alkenyl;
  wherein $L^3$ may be substituted with one or more substituents selected from the group consisting of halo, hydroxy, methoxy and amino ($H_2N$—);
  or $L^3$ is absent; and
$Q^3$ is selected from the group consisting of $C_{1-7}$ alkyl, $C_{1-7}$ haloalkyl, $C_{2-7}$ alkenyl, $C_{3-7}$ cycloalkyl, $C_{5-7}$ cycloalkenyl, aryl, 4-7 membered heterocyclyl, $C_{3-7}$ cycloalkyl-4-7 membered heterocyclyl, 4-7 membered heterocyclyl-$C_{3-7}$ cycloalkyl, bi-(4-7 membered heterocyclyl), $R^{31}HN$—, $R^{31}R^{32}N$—, azinoyl, $C_{3-7}$ cycloalkylamino, 4-7 membered heterocyclylamino, aryl $C_{1-6}$ alkylamino, $C_{3-7}$ cycloalkylsulfanyl, 4-7 membered heterocyclylsulfanyl and 4-7 membered heterocyclyloxy;
  wherein $Q^3$ may be substituted with one or more substituents selected from the group consisting of halo, cyano, hydroxy, $OR^{31}$, $C_{1-5}$ alkyl, $C_{1-5}$ haloalkyl, $C_{2-5}$ alkenyl, nitro, amino, $R^{31}HN$—, $R^{31}R^{32}N$—, amido, $R^{31}HNC(O)$, $R^{31}R^{32}NC(O)$, $R^{31}OC(O)$, $C_{3-7}$ cycloalkyl, monocyclic 4-7 membered heterocyclyl and monocyclic 4-7 membered heterocyclylalkyl, and
  wherein $R^{31}$ and $R^{32}$ are independently $C_{1-5}$ alkyl, $C_{1-5}$ haloalkyl or $C_{2-5}$ alkenyl;
or $A^3$ and $L^3$ are absent and $Q^3$ is sulfanyl;

or a pharmaceutically acceptable ester, ether, N-oxide, amide, salt, hydrate or isotopically labeled form thereof.

Preferred compounds of the present invention are as described in Examples I through V and XI through XVI.

More preferred compounds of the present invention are:

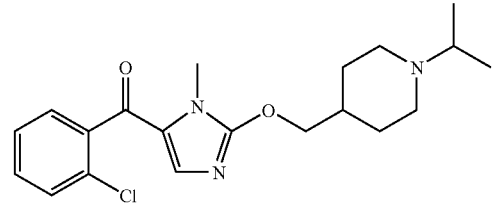

(2-Chlorophenyl)-[2-(1-isopropyl-piperidin-4-ylmethoxy)-3-methyl-3H-imidazol-4-yl]-methanone;

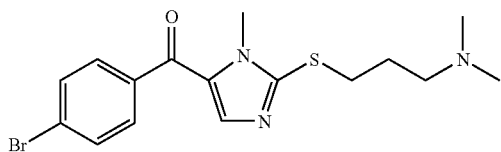

(4-Bromophenyl)-[2-(3-dimethylamino-propylsulfanyl)-3-methyl-3H-imidazol-4-yl]-methanone;

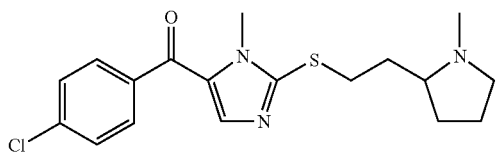

(4-Chlorophenyl)-{3-methyl-2-[2-(1-methylpyrrolidin-2-yl)-ethylsulfanyl]-3H-imidazol-4-yl}-methanone;

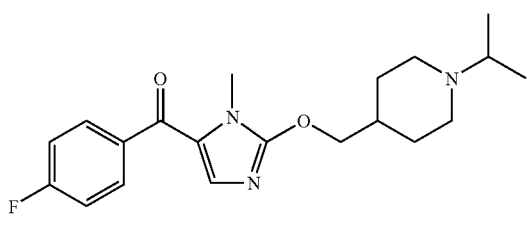

(4-Fluorophenyl)-[2-(1-isopropyl-piperidin-4-ylmethoxy)-3-methyl-3H-imidazol-4-yl]-methanone;

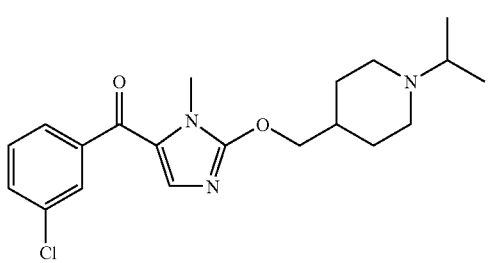

(3-Chlorophenyl)-[2-(1-isopropyl-piperidin-4-ylmethoxy)-3-methyl-3H-imidazol-4-yl]-methanone;

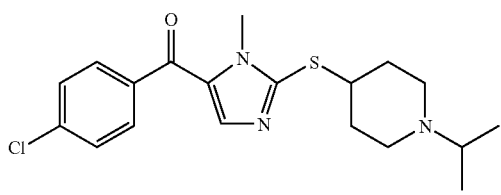

(4-Chlorophenyl)-[2-(1-isopropyl-piperidin-4-ylsulfanyl)-3-methyl-3H-imidazol-4-yl]-methanone;

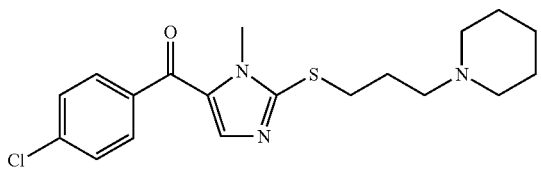

(4-Chlorophenyl)-[3-methyl-2-(3-piperidin-1-yl-propylsulfanyl)-3H-imidazol-4-yl]-methanone;

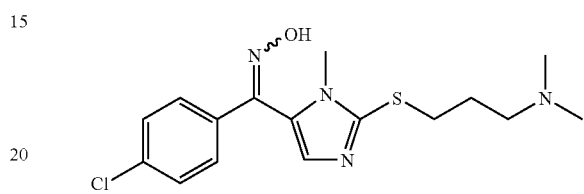

(4-Chlorophenyl)-[2-(3-dimethylamino-propylsulfanyl)-3-methyl-3H-imidazol-4-yl]-methanone oxime;

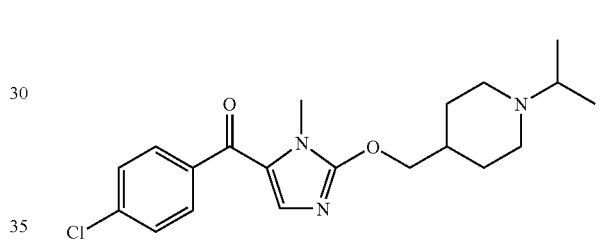

(4-Chlorophenyl)-[2-(1-isopropyl-piperidin-4-ylmethoxy)-3-methyl-3H-imidazol-4-yl]-methanone;

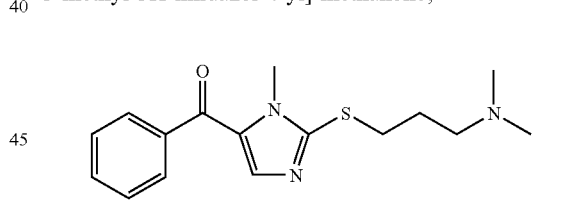

[2-(3-Dimethylamino-propylsulfanyl)-3-methyl-3H-imidazol-4-yl]-phenyl-methanone;

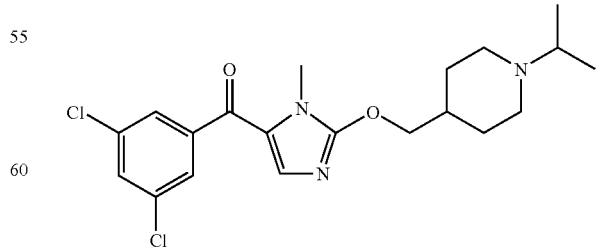

(3,5-Dichlorophenyl)-[2-(1-isopropyl-piperidin-4-ylmethoxy)-3-methyl-3H-imidazol-4-yl]-methanone;

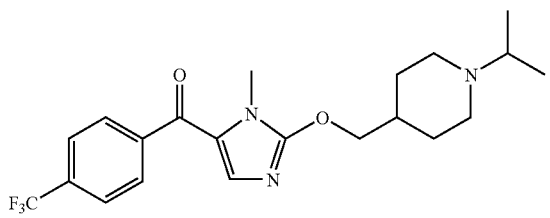

[2-(1-Isopropyl-piperidin-4-ylmethoxy)-3-methyl-3H-imidazol-4-yl]-(4-trifluoromethyl-phenyl)-methanone;

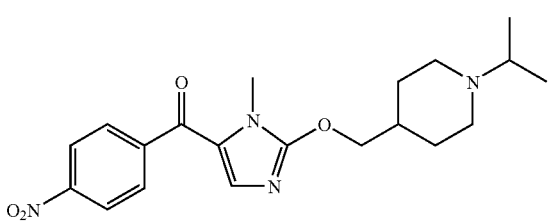

[2-(1-Isopropyl-piperidin-4-ylmethoxy)-3-methyl-3H-imidazol-4-yl]-(4-nitro-phenyl)-methanone;

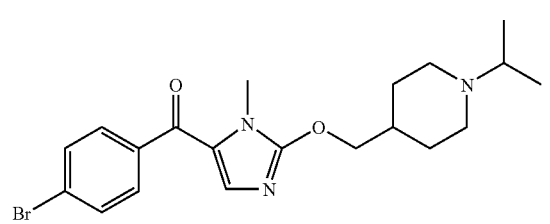

(4-Bromophenyl)-[2-(1-isopropyl-piperidin-4-ylmethoxy)-3-methyl-3H-imidazol-4-yl]-methanone;

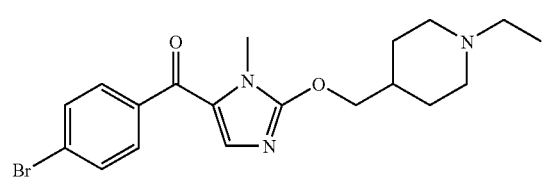

(4-Bromophenyl)-[2-(1-ethyl-piperidin-4-ylmethoxy)-3-methyl-3H-imidazol-4-yl]-methanone;

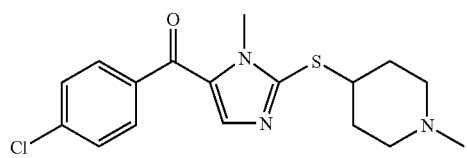

(4-Chlorophenyl)-[3-methyl-2-(1-methyl-piperidin-4-ylsulfanyl)-3H-imidazol-4-yl]-methanone;

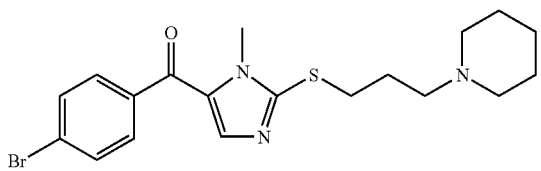

(4-Bromophenyl)-[3-methyl-2-(3-piperidin-1-yl-propylsulfanyl)-3H-imidazol-4-yl methanone;

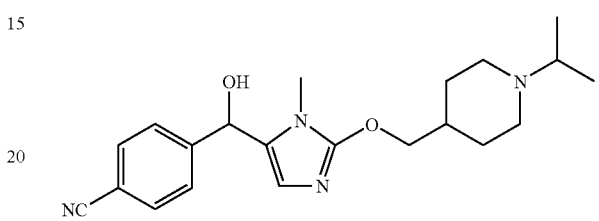

4-{Hydroxy-[2-(1-isopropyl-piperidin-4-ylmethoxy)-3-methyl-3H-imidazol-4-yl]-methyl}-benzonitrile; and

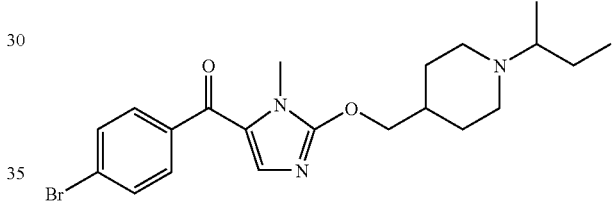

(4-Bromophenyl)-[2-(1-sec-butyl-piperidin-4-ylmethoxy)-3-methyl-3H-imidazol-4-yl]-methanone.

The present invention provides methods for the treatment of disorders and conditions modulated by a histamine receptor, more particularly the $H_3$ receptor, each method comprising administering a disclosed heterocyclic derivative.

Illustrative of the invention is a pharmaceutical composition for the treatment of disorders mediated by the histamine $H_3$ receptor, comprising a pharmaceutically acceptable carrier and a disclosed compound. The invention also provides a process for making a pharmaceutical composition comprising formulating any of the compounds described herein and a pharmaceutically acceptable carrier.

Exemplifying the invention are methods of treating neurologic disorders including sleep wake disturbances, attention deficit hyperactivity disorders and cognitive dysfunction in a subject in need thereof, comprising administering to the subject a therapeutically effective amount of any of the compounds or pharmaceutical compositions described herein.

An example of the invention is a method for treatment of sleep wake disturbances, attention deficit hyperactivity disorders and cognitive dysfunction in a subject in need thereof, comprising administering to the subject an effective amount of any of the compounds or pharmaceutical compositions described herein.

Further illustrating the invention is a method of treating one or more conditions selected from the group consisting of sleep/wake and arousal/vigilance disorders, migraine, neurogenic inflammation, asthma, dementia, mild cognitive impairment (pre-dementia), Alzheimer's disease, epilepsy, narcolepsy, eating disorders, obesity, motion sickness, vertigo, attention deficit hyperactivity disorders, learning and memory disorders, schizophrenia, upper airway allergic response, allergic rhinitis, substance abuse, bipolar disorders, manic disorders and depression in a subject in need thereof, said method comprising administering to the subject a therapeutically effective amount of any of the compounds or pharmaceutical compositions described herein.

Further exemplifying the invention is a method of producing improved alertness or cognition in a subject in need thereof, comprising administering to the subject an effective amount of any of the compounds or pharmaceutical compositions described herein.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts, which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali salts, for example, sodium or potassium salts; alkaline earth salts, for example, calcium or magnesium salts; and salts formed with suitable organic ligands, for example, quaternary ammonium salts. Representative pharmaceutically acceptable salts include the following:

acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

The present invention also provides prodrugs of the compounds of this invention. As used herein, "prodrugs" refer to compounds that are readily convertible in vivo into a compound of Formula I. Thus in the methods of treatment of the present invention, the term "administering" shall encompass the treatment of the various disorders described with the compound specifically disclosed or with a compound that may not be specifically disclosed, but that converts to the specified compound in vivo after administration to the subject. Conventional procedures for the selection and preparation of suitable prodrug derivatives are described, for example, in "Design of Prodrugs", ed. H. Bundgaard, Elsevier, 1985.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. It is also understood that certain compounds of the present invention may possess structural arrangements that permit the structure to exist as tautomers, and as such, these tautomers are intended to be included in the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

As used herein, "halo" or "halogen" shall mean chlorine, bromine, fluorine and iodine.

As used herein, the term "alkyl", whether used alone or as part of a substituent group, shall include unbranched and branched carbon chains, preferably of one to seven carbon atoms and more preferably of one to five carbon atoms, or one to three carbons, that are mono- or di-valent. For example, where an alkyl group has one carbon atom, the term "methyl" is used, which connotes the functional group (—$CH_3$), or (—$CH_2$—), as is chemically appropriate for a given substitution. Alkyl groups include but are not limited to methyl, ethyl, propyl, isopropyl, butyl, isobutyl, sec-butyl, tert-butyl, pentyl and the like.

As used herein, the term "haloalkyl" shall denote unbranched or branched, mono- or di-valent "alkyl" groups substituted with one or more "halo" atoms, preferably one to five "halo" atoms, more preferably one to three "halo" atoms. "Haloalkyl" groups shall include partially and fully halogenated groups and groups with mixed halogens such as —CHCl—$CH_2$Cl, —$CF_3$, —$CFCl_2$, —CH($CH_2$Br)—($CH_2$)$_3$—$CH_2$I and —$CCl_2$—CH($CHCl_2$)—CHCl—.

As used herein, the term "alkenyl", whether used alone or as part of a substituent group, shall include unbranched and branched carbon chains, preferably of two to seven carbon atoms and more preferably of two to five carbon atoms, that are mono- or di-valent. For example, alkenyl groups include vinyl, ethylidine (for example, ethan-1-ylidene and ethan-1-yl-2-ylidene), allyl, pent-3-enyl, pent[3]eno, 3-methylhex-4-enyl, and the like.

As used herein, unless otherwise noted, "alkoxy" shall denote the functional group (R—O—), where R is a monovalent straight or branched chain "alkyl" group as described above. For example, methoxy, ethoxy, n-propoxy, sec-butoxy, tert-butoxy, n-hexyloxy; and the like.

As used herein, unless otherwise noted, "cycloalkyl" shall denote a three- to eight-membered, saturated monocyclic carbocyclic ring structure. Suitable examples include cyclopropyl, cylcobutyl, cyclopentyl, cyclohexyl, cycloheptyl, cyclooctyl, and the like.

As used herein, unless otherwise noted, "cycloalkenyl" shall denote a three- to eight-membered, partially unsaturated, monocyclic, carbocyclic ring structure (preferably a five- to eight-membered, partially unsaturated, monocydlic, carbocyclic ring structure), wherein the ring structure contains at least one double bond. Suitable examples include cyclohexenyl, cyclopentenyl, cycloheptenyl, cyclooctenyl, cyclohexa-1,3-dienyl, and the like.

As used herein, unless otherwise noted, "aryl" shall refer to carbocyclic aromatic groups such as phenyl, naphthyl, (4-phenyl)phenyl and the like.

As used herein, unless otherwise noted, "arylalkyl" shall mean any "alkyl" group substituted with an aryl group such as phenyl, naphthyl, and the like, wherein the arylalkyl group is bound through the alkyl portion. Examples of an arylalkyl are benzyl, phenethyl, and napthylmethyl.

As used herein, unless otherwise noted, the terms "heterocycle", "heterocyclyl" and "heterocyclo" shall denote any three- to eight-membered (preferably four- to seven-membered, and more preferably four- to six-membered) monocyclic, seven- to eleven-membered (preferably eight- to ten-membered) bicyclic, or eleven- to fourteen-membered tricyclic ring structure containing at least one (e.g., between 1 and 2, or between 1 and 3) heteroatom selected from the group consisting of N, O and S, optionally containing one to four (e.g., between 1 and 2, or between 1 and 3) additional heteroatoms, wherein the ring structure is saturated, partially unsaturated, aromatic or partially aromatic. Attachment through any heteroatom or carbon atom of the heterocyclyl group that results in the creation of a stable structure is included within this term.

Exemplary monocyclic heterocyclyl groups can include azetidinyl, thietanyl, pyrrolidyl, pyrrolyl, imidazolinyl, imidazolyl, triazolyl (such as 1H-[1,2,4]triazolyl and 5-oxo-4,5-dihydro-1H-[1,2,4]triazol-3-yl), tetrazolyl, furyl, thienyl, oxazolyl, oxadiazolyl, thiazaolyl, thiadiazolyl, piperidyl, pyridyl, didehydropiperidyl, N-oxo-pyridyl, piperazyl, pyrimidyl, tetrahydropyranyl, morpholinyl, thiomorpholinyl, azepinyl, diazepanyl, and the like.

Exemplary bicyclic heterocyclyl groups can include thienofuryl, pyrrolopyridyl, furopyridyl, thienopyridyl, indolinyl, indolyl, indolizinyl, indazolyl, tetrahydroindazolyl, benzimidazolyl, purinyl, naphthyridinyl, quinolinyl, isoquinolinyl, quinuclidinyl, 3,4-dihydro-4-oxoquinazolinyl, and the like.

Exemplary tricyclic heterocylclyl groups can include carbozolyl, acridyl, phenazyl, phenoxazyl, phenothiazinyl, thianthrenyl, and the like.

As used herein, unless otherwise noted, "heterocyclylalkyl" shall mean any "alkyl" group substituted with a heterocyclyl group such as piperidyl or pyridyl, and the like, wherein the heterocyclylalkyl group is bound to the rest of the molecule through the alkyl portion.

As used herein, unless otherwise noted, the terms "cycloalkyl-heterocyclyl", "heterocyclyl-cycloalkyl", "bi-heterocyclyl" and "biaryl" shall denote independently selected pairs of cyclic systems directly joined to each other by a single bond.

As used herein, unless otherwise noted, the terms "cycloalkylamino", "heterocyclylamino", and "arylalkylamino" shall denote a secondary amino group substituted with cycloalkyl, heterocyclyl, and arylalkyl groups, respectively, wherein the cycloalkylamino, heterocyclylamino, and arylalkylamino substituents are bound through the amino nitrogen. Suitable examples of such substituent groups include, but are not limited to, cyclohexylamino, piperidin-4-ylamino, benzylamino, and the like.

When a particular group is "substituted" (e.g., substituted alkyl, alkenyl, cycloalkyl, aryl, heterocyclyl, or heterocyclyl-alkyl), that group may have one or more substituents, preferably from one to five substituents, more preferably from one to three substituents, most preferably from one to two substituents, independently selected from the list of substituents. Unless otherwise specified, the substituents are independently selected from halo, cyano, $C_{1-5}$ alkyl, trifluoromethyl, hydroxy, hydroxyalkyl, alkoxy, amino, alkylamino, dialkylamino, nitro, aryl, arylalkyl, and the like.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

Under standard nomenclature used throughout this disclosure, the terminal portion of the designated side chain is described first, followed by the adjacent functionality toward the point of attachment. Thus, for example, a "phenyl (alkyl)amido(alkyl)" substituent refers to a group of the formula:

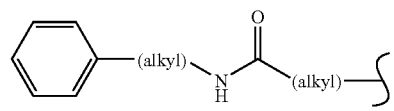

The term "subject" as used herein, refers to an animal, preferably a mammal, most preferably a human, who has been the object of treatment, observation or experiment.

The term "therapeutically effective amount" as used herein, means that amount of active compound or pharmaceutical agent, alone or in combination with another agent according to the particular aspect of the invention, that elicits the biological or medicinal response in a tissue system, animal or human that is being sought by a researcher, veterinarian, medical doctor or other clinician, which includes alleviation of the symptoms of the disease or disorder being treated. For example, a method of treatment relating to a disclosed compound and another compound specified in the claim can include (a) an independently therapeutically effective amount of the disclosed compound and an independently therapeutically effective amount of the specified compound; (b) an independently sub-therapeutically effective amount of a disclosed compound and an independently sub-therapeutically effective amount of the specified compound; or (c) an independently therapeutically effective amount of one compound and an independently sub-therapeutically effective amount of the other compound. The invention features any of the above combinations such that the co-administration steps, the co-administration amounts, or both the steps and the amounts together provide the desired pharmaceutical effect. Advantages of such co-administration can include improvement in the side-effect profiles of one or more of the co-administered agents.

As used herein, the term "composition" is intended to encompass a product comprising the specified ingredients in the specified amounts, as well as any product that results, directly or indirectly, from combinations of the specified ingredients in the specified amounts.

Abbreviations used in the specification, particularly the Schemes and Examples, are as follows:

| | |
|---|---|
| Ac$_2$O | acetic anhydride |
| AcOH | acetic acid |
| t-BOC | Tert-butyloxycarbonyl |
| n-BuLi | n-butyl lithium |
| t-BuLi | tert-butyl lithium |
| BuOH | n- or 1-butanol |
| mCPBA | meta- or 3-chloroperoxybenzoic acid |
| DME | 1,2-dimethoxyethane |
| DMF | N,N-dimethylformamide |
| DMSO | Dimethylsulfoxide |
| Et$_3$N | Triethylamine |
| Et$_2$O | diethyl ether |
| EtOH | Ethanol |
| KOt-Bu | Potassium tert-butoxide |
| LDA | Lithium diisopropylamide |
| LHMDS | Lithium bis(trimethylsilyl)amide |

| | -continued |
|---|---|
| LTMP | Lithium tetramethylpiperidide |
| MeNH$_2$ | Methylamine |
| MeOH | Methanol |
| NaBH(OAc)$_3$ | Sodium triacetoxyborohydride |
| NaOEt | sodium ethoxide |
| NaOMe | Sodium methoxide |
| PCC | Pyridinium chlorochromate |
| PDC | Pyridinium dichromate |
| (Ph$_3$P)$_4$Pd | tetrakis(triphenylphosphine)palladium(0) |
| PhSSPh | Diphenyldisulfide |
| RT | room temperature |
| TFA | Trifluoroacetic acid |
| THF | Tetrahydrofuran |

The compounds of the present invention can be prepared by the following reaction schemes. The starting materials and reagents used in the following schemes are commercially available from such specialty chemical vendors, as Aldrich Chemicals Co., Fluka Chemical Corporation, and the like, or alternatively can be readily prepared by one of ordinary skill in the art. In those cases where a compound can be prepared by more than one reaction scheme of the present invention, the choice of scheme is a matter of discretion that is within the capabilities of one of ordinary skill in the art.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in "Protective Groups in Organic Chemistry", ed. J. F. W. McOmie, Plenum Press, 1973; and T. W. Greene & P. G. M. Wuts, "Protective Groups in Organic Synthesis", 3$^{rd}$ edition, John Wiley & Sons, 1999. The protecting groups may be removed at a convenient subsequent stage using methods known from the art.

Schemes for Synthesizing Compounds of Formula I

This disclosure includes Schemes I, II, III, VII, VIII, IX, X, XI and XII.

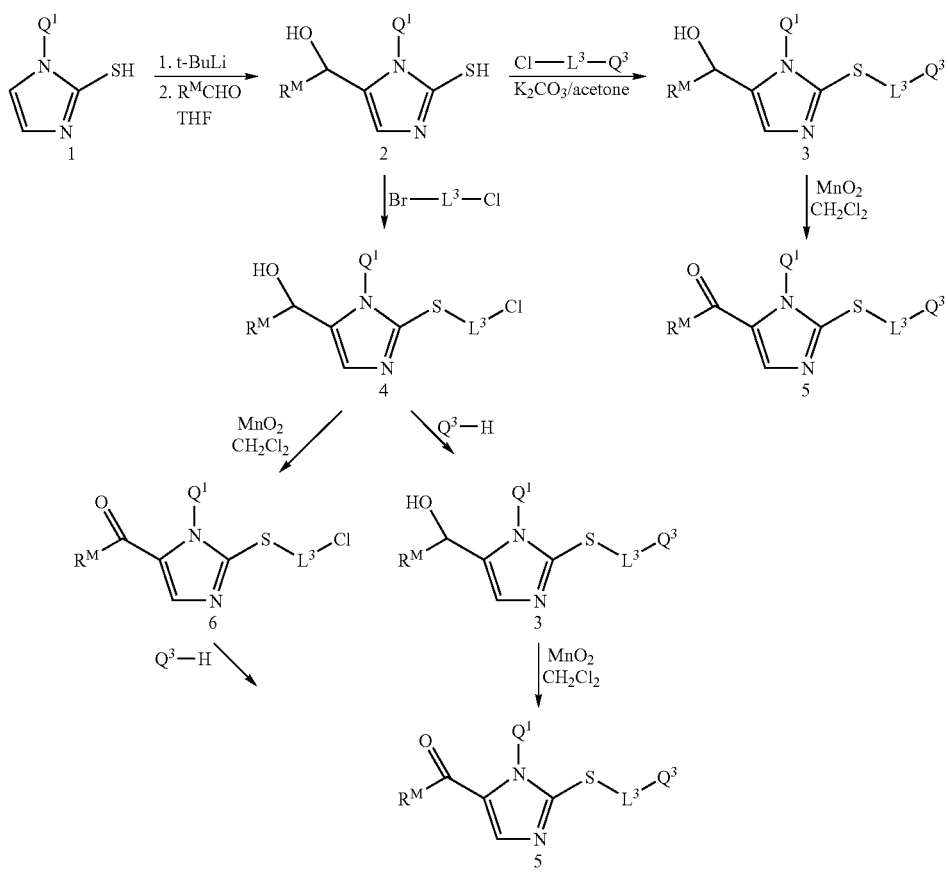

Scheme I

Following Scheme I above, compounds of Formula I of the present invention where M is —C(=O)$R^M$, $A^3$ is sulfur, and $Q^1$, $R^M$, $L^3$ and $Q^3$ are optionally varied, are prepared.

In Scheme I, optionally substituted compound 1 is treated first with a base, preferably an organometallic base (e.g. n-BuLi, LTMP, LDA, LHMDS or, more preferably, t-BuLi), at a low-temperature gradient (preferably from −78° C. to 0° C.) in a solvent such as diethyl ether, benzene, DME or, preferably, THF, and is then treated with aldehyde $R^M$CHO at low temperature (preferably −78° C.) to yield compound 2. Compound 2 is then treated with halide X-$L^3$-$Q^3$, where X is preferably chlorine, in the presence of a base (e.g. NaH, KOH or, preferably, $K_2CO_3$ in acetone) to provide compound 3. Compound 3 is treated with an oxidizing agent (e.g. $KMnO_4$, PCC, PDC, "Swern" oxidation reagents such as $(COCl)_2$/DMSO/$Et_3$N, or, preferably, $MnO_2$ in $CH_2Cl_2$) to yield the desired compound 5 of the present invention. Alternatively, compound 2 may be treated with Br-$L^3$-Cl in the presence of a base (e.g. NaH, KOH or, preferably, $K_2CO_3$ in acetone) to provide compound 4. Compound 4 may be treated with an oxidizing agent, preferably $MnO_2$ in $CH_2Cl_2$, to yield compound 6, which is then treated with primary or secondary amine $Q^3$-H in the presence of a base (e.g. $K_2CO_3$/acetone) to yield the desired compound 5 of the present invention. Alternatively, compound 4 may be treated with primary or secondary amine $Q_3$-H in the presence of a base (e.g. $K_2CO_3$/acetone) to provide compound 3, which is then treated with an oxidizing agent, preferably $MnO_2$ in $CH_2Cl_2$, to again yield the desired compound 5 of the present invention.

THF, then cooled and treated with hydrochloric acid (10%) and potassium thiocyanate to give compound 9. (See R. G. Jones, J. Am. Chem. Soc. 71, 1949, 644.) Compound 9 is then treated with halide X-$L^3$-$Q^3$, where X is preferably chlorine, in the presence of a base (e.g. NaH, KOH or, preferably, $Cs_2CO_3$) to provide the desired compound 5a of the present invention.

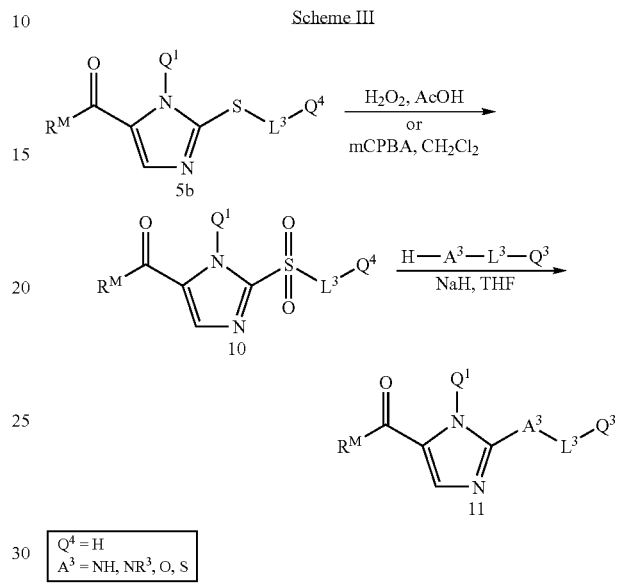

Scheme III

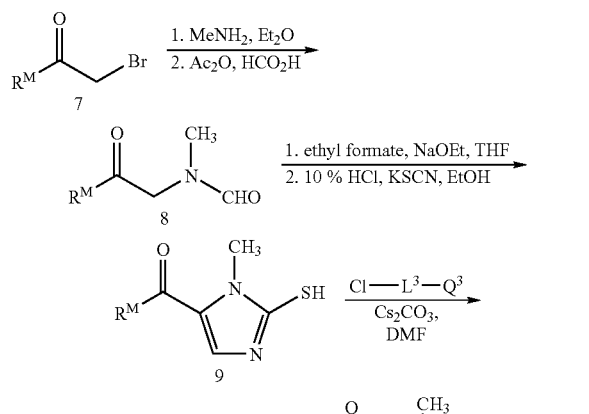

Scheme II

Following Scheme III above, compounds of Formula I of the present invention, where M is —C(=O)$R^M$, $A^3$ is NH, $NR^3$, oxygen or sulfur, and $Q^1$, $R^M$, $L^3$ and $Q^3$ are optionally varied are prepared. The starting material (5b) is prepared using Scheme I. The $L^3$ of the reagent H—$A^3$—$L^3$—$Q^3$ is independent of $L^3$ of formula 5b and formula 10 (both in Scheme III).

In Scheme III, compound 5b (in which $Q^4$ is hydrogen) is treated with an oxidizing agent, preferably hydrogen peroxide in acetic acid or 3-chloroperoxybenzoic acid in dichloromethane or diethyl ether, to provide compound 10. Desired compound 11 of the present invention is obtained upon treatment of compound 10 with H—$A^3$—$L^3$—$Q^3$ in the presence of a base (e.g. KH or, preferably, NaH) in a solvent such as DMF, benzene, DME or, preferably, THF.

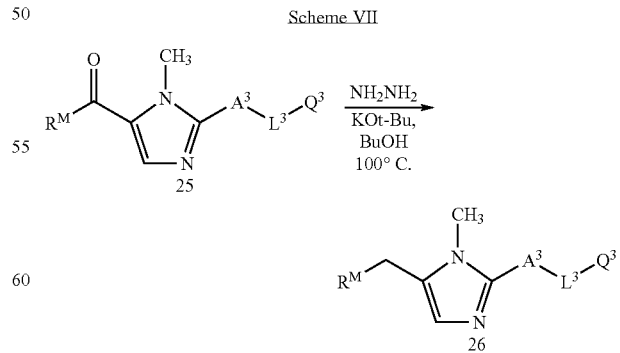

Scheme VII

Following Scheme II above, compounds of Formula I of the present invention, where $Q^1$ is methyl, M is —C(=O)$R^M$, $A^3$ is sulfur, and $R^M$, $L^3$, and $Q^3$ are optionally varied, are prepared.

In Scheme II, alpha-bromoketone 7 is treated with methylamine in diethyl ether, followed by a solution of formyl acetic anhydride (preformed from the reaction of acetic anhydride and formic acid) to afford compound 8. Compound 8 is treated with ethyl formate and an alkoxide (e.g. sodium methoxide, sodium tert-butoxide or, preferably, sodium ethoxide) in a solvent such as benzene or, preferably, Following Scheme VII above, compounds of Formula I of the present invention, where M is —$CH_2R^M$, $Q^1$ is methyl, $A^3$ is sulfur or oxygen, and $R^M$, $L^3$ and $Q^3$ are optionally varied, are prepared. The starting material (25) can be prepared using Schemes I, III, IX or X.

Desired compound 26 of the present invention is obtained upon reduction of compound 25 under "Wolff-Kishner" conditions, that is, treatment with hydrazine in the presence of a base (e.g. KOH, NaOH or, preferably, KOt-Bu) in a solvent such as ethylene glycol or, preferably, butanol at elevated temperature (e.g. 100° C.).

Scheme VIII

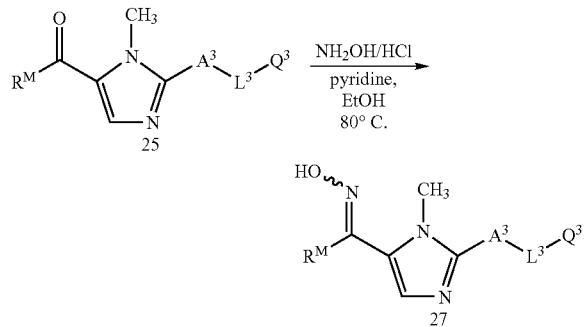

Following Scheme VIII above, compounds of Formula I of the present invention, where M is —C(=N—OH)$R^M$, $Q^1$ is methyl, $A^3$ is sulfur or oxygen, and $L^3$, $Q^3$ and $R^M$ are optionally varied, are prepared. The starting material (25) can be prepared using Schemes I, III, IX or X.

Compound 25 is treated with hydroxylamine hydrochloride in the presence of NaOAc or, preferably, pyridine in an alcoholic solvent (e.g. methanol or, preferably, ethanol) at elevated temperature (e.g. 80° C.) to afford the desired oxime compound 27 of the present invention.

Scheme IX

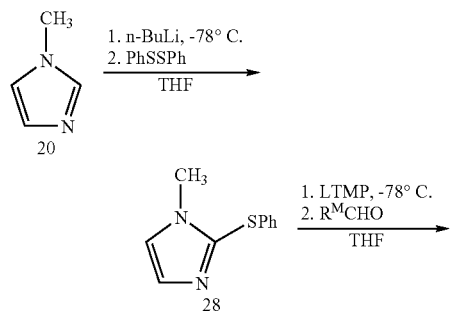

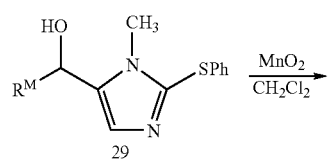

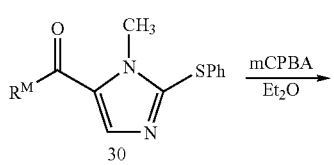

-continued

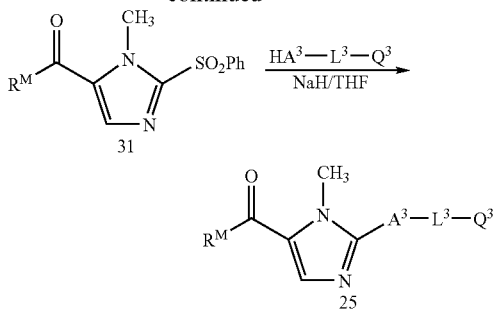

Following Scheme IX above, compounds of Formula I of the present invention, where M is —C(=O)$R^M$, $Q^1$ is methyl, and $A^3$, $L^3$, $Q^3$ and $R^M$ are optionally varied, are prepared.

Compound 20 is treated with an organolithium base (e.g. LDA, t-BuLi or, preferably, n-BuLi) at low temperature (preferably −78° C.) in a solvent such as DME, diethyl ether or, preferably, THF, followed by treatment with an organodisulfide, preferably diphenyldisulfide, to afford compound 28. Compound 29 is obtained by treating compound 28 with a base (e.g. LHMDS, LDA or, preferably, LTMP) at low temperature (preferably −78° C.) in a solvent such as THF, followed by aldehyde $R^M$CHO. Compound 29 is treated with an oxidizing agent (e.g. KMnO$_4$, PCC, PDC, "Swern" oxidation reagents such as (COCl)$_2$/DMSO/Et$_3$N or, preferably, MnO$_2$ in CH$_2$Cl$_2$) to yield compound 30, which is treated with an oxidizing agent (e.g. hydrogen peroxide in acetic acid, 3-chloroperoxybenzoic acid in dichloromethane, or, preferably, 3-chloroperoxybenzoic acid in diethyl ether) to provide compound 31. Desired compound 25 of the present invention is obtained upon treatment of compound 31 with H—$A^3$—$L^3$—$Q^3$ in the presence of a base (e.g. KH or, preferably, NaH) in a solvent such as DMF, benzene, DME or, preferably, THF.

Scheme X

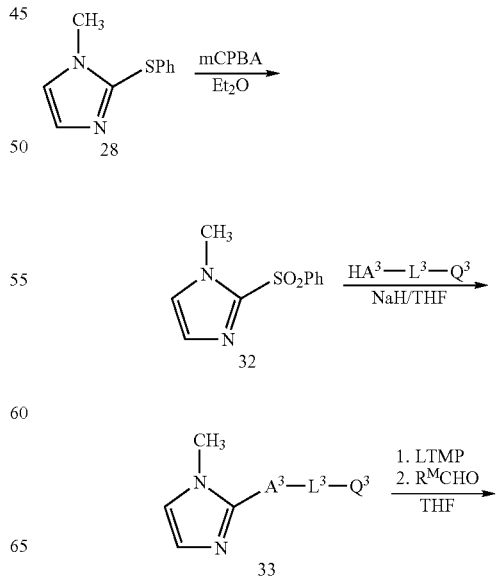

-continued

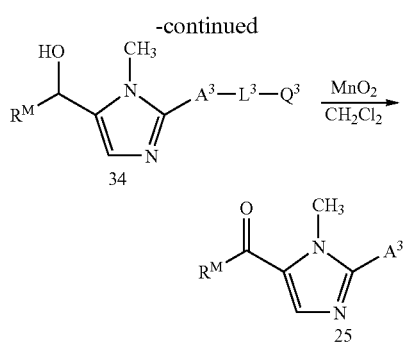

Following Scheme X above, compounds of Formula I of the present invention, where M is —C(=O)$R^M$, $Q^1$ is methyl, and $A^3$, $L^3$, $Q^3$, and $R^M$ are optionally varied, are prepared. The starting material is compound 28 from Scheme IX.

Compound 28 is treated with an oxidizing agent (e.g. hydrogen peroxide in acetic acid or, preferably, 3-chloroperoxybenzoic acid in diethyl ether) to provide compound 32. Compound 33 is obtained upon treatment of compound 32 with H—$A^3$—$L^3$—$Q^3$ in the presence of a base (e.g. KH or, preferably, NaH) in a solvent such as DMF, benzene, DME or, preferably, THF. Compound 34 is obtained by treating compound 33 with a base (e.g. LHMDS, LDA or, preferably, LTMP) at low temperature (preferably −78° C.) in a solvent such as THF, followed by aldehyde $R^M$CHO. Compound 34 is treated with an oxidizing agent (e.g. KMnO$_4$, PCC, PDC, "Swern" oxidation reagents such as (COCl)$_2$/DMSO/Et$_3$N or, preferably, MnO$_2$ in CH$_2$Cl$_2$) to yield the desired compound 25 of the present invention.

Scheme XI

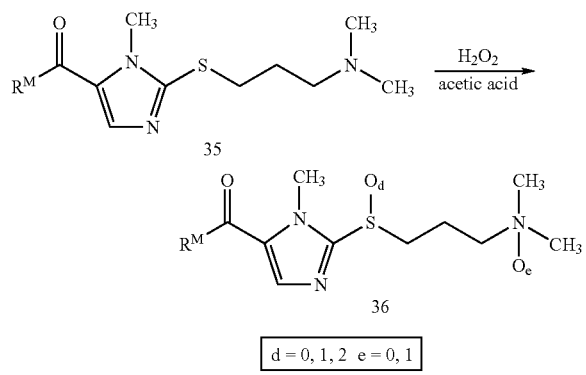

d = 0, 1, 2  e = 0, 1

Following Scheme XI above, compounds of Formula I of the present invention, where M is —C(=O)$R^M$, $Q^1$ is methyl, $A^3$ is sulfur, sulfoxide or sulfone, $L^3$ is n-propyl, $Q^3$ is dimethylamino or dimethylazinoyl and $R^M$ is optionally varied, are prepared. In general, the starting material (35), is prepared using Scheme X to provide appropriately substituted 25 (i.e. compound 35). Where $R^M$ is hydrogen, compound 35 is obtained directly from 33 in Scheme X by treatment of the latter with 1) LTMP and 2) DMF. Starting material may also be prepared using Schemes I or III.

Compound 35 is treated with hydrogen peroxide in acetic acid to provide desired compounds 36 of the present invention as a mixture of desired oxidation states. The product mixture is separated by chromatography (e.g. flash chromatography on silica gel).

Scheme XII

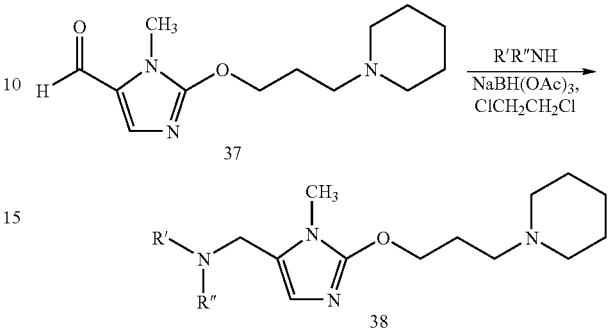

Following Scheme XII above, compounds of Formula I of the present invention, where M is CH$_2$$R^M$, $R^M$ is optionally substituted —NR'R" (where R' and R" are independently C$_{1-7}$ alkyl or, taken together with the nitrogen to which they are attached, form a four- to seven-membered nitrogen heterocycle), $Q^1$ is methyl, $A^3$ is oxygen, $L^3$ is n-propyl and $Q^3$ is N-piperidyl, are prepared. The starting material, compound 37, is prepared using Scheme X to provide appropriately substituted 33 (i.e. $A^3$ is oxygen, $L^3$ is n-propyl and $Q^3$ is N-piperidyl). Compound 37 is then obtained directly from 33 in Scheme X by treatment of the latter with 1) LTMP and 2) DMF.

Desired compound 38 of the present invention is obtained by treating compound 37 with an amine in the presence of a reducing agent such as NaBH$_3$CN or, preferably, NaBH(OAc)$_3$ in a solvent such as methanol, ethanol, CF$_3$CH$_2$OH or, preferably, 1,2-dichloroethane.

The present invention provides a series of heterocyclic derivatives with the ability to modulate the activity of a histamine receptor, specifically the H$_3$ receptor. These heterocycles include N(1)-substituted imidazoles that contain both 2- and 5-substituents.

Imidazole:

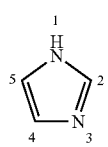

A number of compounds of the present invention that are methylated at the N(1) position of the imidazole ring have been found to have exceptional activity.

The histamine H$_3$ receptor binding effectiveness of compounds of the present invention was determined using the human histamine H$_3$ receptor, Lovenberg et al *Mol. Pharmacol*. 1999, 1107. Screening using the human receptor is particularly important for the identification of new therapies for the treatment of human disease. Prior binding assays, for example, relied on rat synaptosomes (Garbarg et al *J. Pharmacol. Exp. Ther*. 1992, 263, 304), rat cortical membranes (West et al Mol. Pharmacol. 1990, 610), and guinea pig brain (Korte et al *Biochem. Biophys. Res. Commun*. 1990, 978). A recent comparative study comparing human H₃ receptor activity with H₃ receptors from rodent and primate have shown significant differences in the respective pharmacology of the rodent and primate receptors to the human receptor. (West et al *Eur. J. Pharmacol.* 1999, 233; Lovenberg et al., *J. Pharmacol. Exp. Ther.* 2000, 293, 771-778.)

The present invention also provides methods useful for the treatment of diseases or conditions that are modulated by the histamine H₃ receptor including, but not limited to, sleep/wake and arousal/vigilance disorders, migraine, asthma, dementia, mild cognitive impairment (pre-dementia), Alzheimer's disease, epilepsy, narcolepsy, eating disorders, obesity, motion sickness, vertigo, attention deficit hyperactivity disorders, learning and memory disorders, schizophrenia, upper airway allergic response, allergic rhinitis, substance abuse, bipolar disorders, manic disorders and depression.

The present invention also provides compositions and methods useful for the treatment of disorders or conditions modulated by the histamine H₃ receptor in combination with compounds that modulate other receptors including, but not limited to, histamine H₁ and histamine H₂ receptors. The compounds, compositions and methods of the present invention are also useful in the treatment of diseases or conditions modulated by the histamine H₃ receptor (such as depression or other CNS disorders) in combination with compounds that are selective serotonin re-uptake inhibitors (SSRIs), such as PROZAC™, and selective norepinephrine uptake inhibitors.

The present invention provides methods for treating various disorders associated with histamine H₃ antagonist activity by administering a therapeutically effective amount of a compound of the present invention, or a composition comprising said compound, to a subject in need of such treatment. Also included in the present invention are methods of co-administration, comprising administering at least one disclosed compound and administering at least one agent selected from a histamine H₃ receptor modulating compound, a histamine H₂ receptor modulating compound, an SSRI (such as PROZAC™), and a selective norepinephrine uptake inhibiting compound; and combination compositions thereof. Co-administration includes essentially simultaneous administration of either a co-formulated combination or separate formulations, and administration of separate formulations at different times.

The present invention provides a method of treating disorders and conditions mediated by the H₃ receptor, particularly a method of treating attention deficit hyperactivity disorder (ADHD) (i.e. improving attention and/or memory retention), in a subject in need thereof that comprises administering any of the compounds as defined herein in a therapeutically effective amount. The compound may be administered to a subject by any conventional route of administration, including, but not limited to, intravenous, oral, subcutaneous, intramuscular, intradermal and parenteral. The quantity of the compound that is effective for treating ADHD is between 0.01 mg per kg and 20 mg per kg of subject body weight.

The present invention provides a method for treating dementia and/or Alzheimer's disease, wherein a compound of the present invention acts as a histamine H₃ antagonist (Panula et al *Abstr. Society Neuroscience*, 1995, 21, 1977).

The present invention provides a method for treating epilepsy according to (Yokoyama et al *Eur. J. Pharmacol.*, 1993, 234, 129), wherein a compound of the present invention acts as a histamine H₃ antagonist.

The present invention provides a method for treating narcolepsy and/or eating disorders based on the reference, Machidori et al *Brain Research* 1992, 590, 180, where a compound of the present invention acts as a histamine H₃ antagonist.

The present invention provides a method for treating one or more disorders or conditions selected from a group consisting of motion sickness, vertigo, attention deficit hyperactivity disorders (ADHD), and learning and memory disorders, wherein a compound of the present invention acts as a histamine H₃ antagonist, based on the reference, Barnes et al *Abstr. Society Neuroscience*, 1993, 19, 1813.

The present invention provides a method for treating schizophrenia based on the reference, Schlicker et al *Naunyn-Schmiedeberg's Arch. Pharmacol.*, 1996, 353, 290-294, wherein a compound of the present invention acts as a histamine H₃ antagonist.

The present invention provides a method of treating upper airway allergic response by administering a compound of the present invention alone, or in combination with a histamine H₃ antagonist. Such utility is reported in U.S. Pat. Nos. 5,217,986; 5,352,707 and 5,869,479.

The present invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, autoinjector devices or suppositories; for oral, parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 1 to about 1000 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin. For parenteral administration, sterile suspensions and solutions are desired. Isotonic preparations which generally contain suitable preservatives are employed when intravenous administration is desired.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phophatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyl-eneoxidepolyl-ysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxy butyric acid, polyesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of disorders or conditions mediated by the histamine $H_3$ receptor (e.g. ADHD) is required.

The daily dosage of the products may be varied over a wide range from 1 to 1,000 mg per adult human per day. For oral administration, the compositions are preferably provided in the form of tablets containing, 1.0, 5.0, 10.0, 15.0, 25.0, 50.0, 100, 250 and 500 milligrams of the active ingredient for the symptomatic adjustment of the dosage to the subject to be treated. An effective amount of the drug is ordinarily supplied at a dosage level of from about 0.01 mg/kg to about 20 mg/kg of body weight per day. Preferably, the range is from about 0.02 mg/kg to about 10 mg/kg of body weight per day, and especially from about 0.05 mg/kg to about 10 mg/kg of body weight per day. The compounds may be administered on a regimen of 1 to 4 times per day.

Optimal dosages to be administered may be readily determined by those skilled in the art, and will vary with the particular compound used, the strength of the preparation, the mode of administration, and the advancement of the disease condition. In addition, factors associated with the particular subject being treated, including subject age, weight, diet and time of administration, will result in the need to adjust dosages.

The methods of treatment described in the present invention (e.g. that of ADHD) may also be carried out using a pharmaceutical composition comprising any of the compounds as defined herein and a pharmaceutically acceptable carrier. The pharmaceutical composition may contain between about 5 mg and 1000 mg, preferably about 10 to 500 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

The present invention also provides isotopically labeled compounds useful for positron emission tomography (PET), a non-invasive in vivo imaging technique, and/or for absorption/distribution/metabolism/excretion (ADME) studies. Positron emission tomography uses positron emitting radioisotopes as molecular probes. When a compound containing positron emitting nuclides, such as $^{11}C$, $^{13}N$, $^{15}O$ or $^{18}F$, is administered to a subject, annihilation radiation can be detected electronically using a coincidence technique. PET measurements can, for example, provide information about the location and density of receptors. (Phelps, M. E. *Proc. Natl. Acad. Sci.*, 2000, 97, 9226-9233) In the present invention, an appropriately labeled compound provides a useful molecular probe and diagnostic tool for studying central nervous system (CNS) disorders. Of particular interest are 18F-labeled compounds, which may be prepared from nitro-substituted, electron-deficient phenyl precursors by nucleophilic aromatic substitution using [$^{18}F$]fluoride ion. Nucleophilic fluorinations may be performed under anhydrous conditions in an inert atmosphere in a non-hydrolytic solvent, usually in the presence of a phase transfer agent, for example, Kryptofix 2.2.2® or tetra-N-butylammonium hydrogen carbonate. (Ding, Y.-S. et al *J. Med. Chem.*, 1991, 34, 767-771)

References are cited throughout the specification. These references in their entirety are incorporated by reference into the specification to more fully describe the state of the art to which it pertains.

The following examples (Examples I, II, III, IV, V, XI, XII, XIII, XIV, XV, XVI and XVIII) are intended to illustrate but not limit the invention.

EXAMPLES

Example I

Preparation of (4-Chloro-phenyl)-[2-(2-dimethylamino-ethylsulfanyl)-3-methyl-3H-imidazol-4-yl]methanone

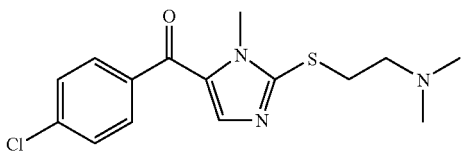

This example teaches the preparation of a compound of Formula I following Scheme I, wherein M is —C(=O)$R^M$; $R^M$ is p-chlorophenyl; $A^3$ is sulfur; $L^3$ is ethyl; $Q^3$ is dimethylamino; and $Q^1$ is methyl.

Step A: Preparation of (4-Chlorophenyl)-(2-mercapto-3-methyl-3H-imidazol-4-yl)-methanol

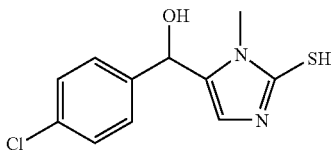

2-Mercapto-1-methylimidazole (1.0 g) in THF (30 mL) under dry nitrogen at −78° C. was treated with 1.7M (in pentane) t-butyl lithium (11.3 mL). After stirring for 15 min, the reaction mixture was warmed to 0° C. After 30 min, the reaction was cooled to −78° C. and, 4-chlorobenzaldehyde (1.5 g) in THF (20 mL) was added dropwise. After 1 h, the reaction was quenched with brine (100 mL) and slowly warmed to room temperature. This mixture was partitioned between diethyl ether (100 mL) and water (25 mL). The organic portion was separated, washed with brine (50 mL), dried over magnesium sulfate, filtered and evaporated. The residue was suspended in diethyl ether and filtered off to provide as a white powder (4.4 g, 66%) the compound of Formla I wherein M is —CHOHR$^M$; A$^M$ is hydroxy; R$^M$ is p-chlorophenyl; A$^3$ is thiol (SH); L$^3$ is absent; Q$^3$ is absent; and Q$^1$ is methyl; also known as, (4-Chlorophenyl)-(2-mercapto-3-methyl-3H-imidazol-4-yl)-methanol. M calc=254; M+H found=255.

Calculated for $C_{11}H_{11}N_2OSCl$: C, 51.87; H, 4.35; N, 11.00; found C, 51.97; H, 4.25; N, 10.81.

Step B: Preparation of (4-Chlorophenyl)-[2-(2-dimethylamino-ethylsulfanyl)-3-methyl-3H-imidazol-4-yl]-methanol

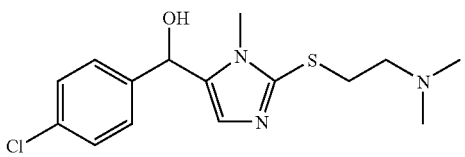

The product from Example I, Step A (0.1 g) in acetone (4 mL) was treated with potassium carbonate (0.5 g) followed by dimethylaminoethyl chloride (0.2 g). The mixture was allowed to stir at room temperature for 16 h and was then partitioned between ethyl acetate (50 mL) and brine (50 mL). The organic layer was separated and washed with brine (2×200 mL), dried over sodium sulfate, filtered, and evaporated to give the crude product. The crude product was purified by silica gel chromatography using 2% Methanol/Dichloromethane as the eluent to provide 0.08 g (69% yield) of the compound of Formula I wherein M is —CHOHR$^M$; A$^M$ is hydroxy; R$^M$ is p-chlorophenyl; A$^3$ is sulfur; L$^3$ is ethyl; Q$^3$ is dimethylamino; and Q$^1$ is methyl; also known as, (4-Chlorophenyl)-[2-(2-dimethylamino-ethylsulfanyl)-3-methyl-3H-imidazol-4-yl]-methanol. M calc=325; M+H found=326.

Step C: Preparation of (4-Chlorophenyl)-[2-(2-dimethylamino-ethylsulfanyl)-3-methyl-3H-imidazol-4-yl]methanone The product of Example I, Step B (0.07 g) in dichloromethane (2 mL) was treated with MnO$_2$ (0.05 g). The reaction mixture was allowed to stir at room temperature for 1 h. The mixture was filtered through a pad of diatomaceous earth (5 g) and concentrated to provide (4-Chloro-phenyl)-[2-(2-dimethylamino-ethylsulfanyl)-3-methyl-3H-imidazol-4-yl]-methanone (0.06 g, 87%), M calc 323, M+H found=324; $^1$H NMR (400 MHz, CDCl$_3$): δ 7.78-7.66 (dm, J=8.5 Hz, 2H), 7.42 (s, 1H), 7.41-7.36 (dm, J=8.7 Hz, 2H), 3.82 (s, 3H), 3.38 (t, J=6.7 Hz, 2H), 2.64 (t, J=6.7 Hz, 2H), 2.25 (s, 6H). The compound demonstrated useful biological activity when assessed with a [$^3$H]-N-methylhistamine binding assay (see Table in Example XVIII).

Step D: Additional Compounds Prepared Following Scheme I and Example I, Steps A, B, and C.

The following compounds of Formula I were prepared following Scheme I and Example I, Steps A, B, and C; and substituting reagents, and adjusting reaction conditions as needed. The compounds were found to have useful biological activity based on the K$_i$(nM) value from a [$^3$H]-N-methylhistamine binding assay.

The compounds of Formula I, wherein:

M is —CHOHR$^M$; A$^M$ is hydroxy; R$^M$ is p-chlorophenyl; A$^3$ is sulfur; L$^3$ is n-propyl; Q$^3$ is dimethylamino; and Q$^1$ is methyl; also known as, (4-Chlorophenyl)-[2-(3-dimethylamino-propylsulfanyl)-3-methyl-3H-imidazol-4-yl]-methanol; M calc=339; M+H found=340; $^1$H NMR (400 MHz, CDCl$_3$): δ 7.26-7-7.20 (m, 4H), 6.44 (s, 1H), 5.67 (s, 1H), 3.43 (s, 3H), 2.91 (t, J=7.2 Hz, 2H), 2.25-2.21 (t, J=7.4 Hz, 2H), 2.05 (s, 6H), 1.71-1.60 (m, 2H);

M is —CHOHR$^M$; A$^M$ is hydroxy; R$^M$ is p-bromophenyl; A$^3$ is thiol (SH); L$^3$ is absent; Q$^3$ is absent; and Q$^1$ is methyl; also known as, (4-Bromophenyl)-(2-mercapto-3-methyl-3H-imidazol-4-yl)-methanol; M calc=298; M$^-$ found=298;

M is —CHOHR$^M$; A$^M$ is hydroxy; R$^M$ is p-chlorophenyl; A$^3$ is sulfur; L$^3$ is absent; Q$^3$ is 4-methylpentyl; and Q$^1$ is methyl; also known as, (4-Chlorophenyl)-[3-methyl-2-(4-methylpentylsulfanyl)-3H-imidazol-4-yl]-methanol; M calc=338; M+H found=339;

M is —C(=O)R$^M$; R$^M$ is p-chlorophenyl; A$^3$ is sulfur; L$^3$ is absent; Q$^3$ is 4-methylpentyl; and Q$^1$ is methyl; also known as, (4-Chlorophenyl)-[3-methyl-2-(4-methylpentylsulfanyl)-3H-imidazol-4-yl]-methanone; M calc=336; M+H found=337;

M is —CHOHR$^M$; A$^M$ is hydroxy; R$^M$ is p-chlorophenyl; A$^3$ is sulfur; L$^3$ is n-propyl; Q$^3$ is 1-piperidyl; and Q$^1$ is methyl; also known as, (4-Chlorophenyl)-[3-methyl-2-(3-piperidin-1-yl-propylsulfanyl)-3H-imidazol-4-yl]-methanol; M calc=379; M+H found=380; $^1$H NMR (400 MHz, CDCl$_3$): δ 7.32 (s, 4H), 6.55 (s, 1H), 5.77 (s, 1H), 3.57 (s, 3H), 3.00 (t, J=7.1 Hz, 2H), 2.34 (m, 6), 1.80 (m, 2H), 1.55 (m, 4H), 1.26 (br m, 2H);

M is —CHOHR$^M$; A$^M$ is hydroxy; R$^M$ is p-chlorophenyl; A$^3$ is sulfur; L$^3$ is ethyl; Q$^3$ is tetrahydropyran-2-yloxy; and Q$^1$ is methyl; also known as, (4-Chloro-phenyl)-{3-methyl-2-[2-(tetrahydropyran-2-yloxy)-ethylsulfanyl]-3H-imidazol-4-yl}-methanol; M calc=382; M+H found=383; $^1$H NMR (400 MHz, CDCl$_3$): δ 7.35-7.29 (m, 4H), 6.52 (s, 1H), 5.78 (s, 1H), 4.59-4.54 (m, 1H), 3.93-3.77 (m, 2H), 3.65-3.56 (m, 1H), 3.49-3.40 (m, 1H), 3.49 (s, 3H), 3.22 (t, J=6.6 Hz, 2H), 1.85-1.72 (m, 1H), 1.72-1.61 (m, 1H), 1.60-1.45 (m, 4H);

M is —CHOHR$^M$; A$^M$ is hydroxy; R$^M$ is p-chlorophenyl; A$^3$ is sulfur; L$^3$ is absent; Q$^3$ is 2-hydroxyethyl; and Q$^1$ is methyl; also known as, 2-{5-[(4-Chlorophenyl)-hydroxymethyl]-1-methyl-1H-imidazol-2-ylsulfanyl}-ethanol; M calc=298; M+H found=299;

M is —CHOHR$^M$; A$^M$ is hydroxy; R$^M$ is p-chlorophenyl; A$^3$ is sulfur; L$^3$ is ethyl; Q$^3$ is cyclohexylsulfanyl; and Q$^1$ is methyl; also known as, (4-Chloro-phenyl)-[2-(2-cyclohexylsulfanyl-ethylsulfanyl)-3-methyl-3H-imidazol-4-yl]-methanol; M calc=396; M+H found=397;

M is —C(=O)R$^M$; R$^M$ is p-chlorophenyl; A$^3$ is sulfur; L$^3$ is ethyl; Q$^3$ is tetrahydropyran-2-yloxy; and Q$^1$ is methyl; also known as, (4-Chloro-phenyl)-{3-methyl-2-[2-(tetrahydropyran-2-yloxy)-ethylsulfanyl]-3H-imidazol-4-yl}-methanone; M calc=380; M+H found=381;

M is —C(=O)R$^M$; R$^M$ is p-chlorophenyl; A$^3$ is sulfur; L$^3$ is absent; Q$^3$ is 2-hydroxyethyl; and Q$^1$ is methyl; also known as, (4-Chlorophenyl)-[2-(2-hydroxyethylsulfanyl)-3-methyl-3H-imidazol-4-yl]-methanone; M calc=296; M+H found=297;

M is —C(=O)R$^M$; R$^M$ is p-chlorophenyl; A$^3$ is sulfur; L$^3$ is ethyl; Q$^3$ is cyclohexylsulfanyl; and Q$^1$ is methyl; also known as, (4-Chloro-phenyl)-[2-(2-cyclohexylsufanyl-ethylsulfanyl)-3-methyl-3H-imidazol-4-yl]-methanone; $^1$H NMR (400 MHz, CDCl$_3$): δ 7.70 (dm), 7.39 (dm), 3.82 (s), 3.41-3.38 (m), 2.90-2.81 (m); and M is hydrogen; A$^3$ is sulfur; L$^3$ is n-propyl; Q$^3$ is dimethylamino; and Q$^1$ is methyl; also known as, Dimethyl-[3-(1-methyl-1H-imidazol-2-ylsulfanyl)-propyl]-amine; M calc=199; M+H found=200.

Example II

Preparation of (4-Chlorophenyl)-[2-(3-dimethylamino-propylsulfanyl)-3-methyl-3H-imidazol-4-yl]-methanone

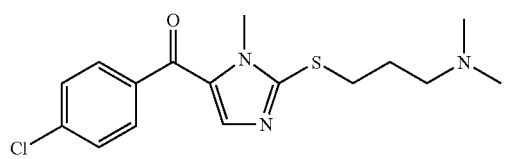

This example demonstrates the preparation of a compound of Formula I following Scheme I, wherein M is —C(=O)R$^M$; R$^M$ is p-chlorophenyl; A$^3$ is sulfur; L$^3$ is n-propyl; Q$^3$ is dimethylamino; and Q$^1$ is methyl. Alternatively, this compound can be prepared following Schemes II, IX, and X.

Step A: Preparation of (4-Chlorophenyl)-[2-(3-chloro-propylsulfanyl)-3-methyl-3H-imidazol-4-yl]-methanol

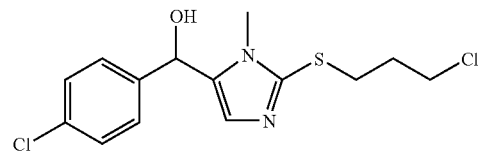

The product of example 1, Step A (0.09 g) in acetone (2 mL) and N,N-dimethylformamide (2 mL) was treated with potassium carbonate (0.2 g) followed by 1-bromo-3-chloropropane (0.11 g). The mixture was allowed to stir at room temperature for 16 h and was then partitioned between ethyl acetate (50 mL) and brine (50 mL). The organic layer was separated and washed with brine (2×200 mL), dried over sodium sulfate, filtered, and evaporated to give the crude product. The crude product was purified by silica gel chromatography using 2-5% Methanol/Dichloromethane as the eluent to provide (4-Chloro-phenyl)-[2-(3-chloro-propylsulfanyl)-3-methyl-3H-imidazol-4-yl]-methanol (0.08 g, 69%); M calc=330; M+H found=331.

Step B: Preparation of (4-Chloro-phenyl)-[2-(3-chloro-propylsulfanyl)-3-methyl-3H-imidazol-4-yl]-methanone

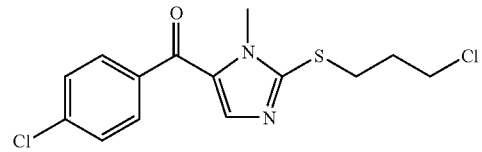

The product of Example II, Step A (2.1 g) was subjected to the same conditions as described in Example I, Step C (MnO$_2$, 0.3 g) to provide (4-Chloro-phenyl)-[2-(3-chloro-propylsulfanyl)-3-methyl-3H-imidazol-4-yl]-methanone (1.7 g, 81%).

Step C: Preparation of (4-Chloro-phenyl)-[2-(3-dimethylamino-propylsulfanyl)-3-methyl-3H-imidazol-4-yl]methanone The product from Example II, Step B (0.42 g) in acetone (25 mL) was treated with potassium carbonate followed by dimethylamine hydrochloride (0.42 g). The mixture was allowed to stir at 60° C. overnight. The reaction mixture was cooled to room temperature and diluted with ethyl acetate (75 mL) and washed with brine (2×70 mL). The organic portion was dried over magnesium sulfate, filtered, and concentrated to give the crude product. The crude was purified by silica gel chromatography (1-10% methanol (2M ammonia)/dichloromethane) to provide (4-Chlorophenyl)-[2-(3-dimethylamino-propylsulfanyl)-3-methyl-3H-imidazol-4-yl]-methanone (25 mg, 6%), M calc=337, M+H found=338; $^1$H NMR (400 MHz, CDCl$_3$): δ 7.81-7.73 (dm, J=8.5 Hz, 2H), 7.50 (s, 1H), 7.48-7.44 (dm, J=8.6 Hz, 2H), 3.91 (s, 3H), 3.33 (t, J=7.1 Hz, 2H), 2.45 (t, J=7.1 Hz, 2H), 2.27 (s, 6H), 2.0-1.91 (m, 2H). The compound demonstrated useful biological activity when assessed with a [$^3$H]-N-methylhistamine binding assay (see Table in Example XVIII).

Step D: Additional Compounds Prepared Following Scheme I and Example II, Steps A, B, and C.

The following compounds of Formula I were prepared following Scheme I and Example II, Steps A, B, and C; and substituting reagents, and adjusting reaction conditions as needed. The compounds were found to have useful biological activity based on the $K_i$(nM) value from a [$^3$H]-N-methylhistamine binding assay.

The compounds of Formula I wherein:

M is —CHOHR$^M$; A$^M$ is hydroxy; R$^M$ is p-bromophenyl; A$^3$ is sulfur; L$^3$ is absent; Q$^3$ is 3-chloropropyl; and Q$^1$ is methyl; also known as, (4-Bromophenyl)-[2-(3-chloro-propylsulfanyl)-3-methyl-3H-imidazol-4-yl]-methanol; M calc=374; M+H found=375;

M is —CHOHR$^M$; A$^M$ is hydroxy; R$^M$ is p-bromophenyl; A$^3$ is sulfur; L$^3$ is n-propyl; Q$^3$ is 1-piperidyl; and Q$^1$ is methyl; also known as, (4-Bromophenyl)-[3-methyl-2-(3-piperidin-1-yl-propylsulfanyl)-3H-imidazol-4-yl]-methanol; M calc=423; M+H found=424; $^1$H NMR (400 MHz, CDCl$_3$): δ 7.41 (dd, J=8.6, 2.0 Hz, 2H), 7.2 (d, J=8.3 Hz, 2H), 6.5 (s, 1H), 5.69 (s, 1H), 3.39 (s, 3H), 2.94 (t, J=7.1 Hz, 2H), 2.26 (m, 6H), 1.72 (m, 2H), 1.47 (m, 4H), 1.34 (br m, 2H);

M is —CHOHR$^M$; A$^M$ is hydroxy; R$^M$ is p-chlorophenyl; A$^3$ is sulfur; L$^3$ is n-propyl; Q$^3$ is 4-morpholinyl; and Q$^1$ is methyl; also known as, (4-Chlorophenyl)-[3-methyl-2-(3-morpholin-4-yl-propylsulfanyl)-3H-imidazol-4-yl]-methanol; M calc=381; M+H found=382;

M is —C(═O)R$^M$; R$^M$ is p-chlorophenyl; A$^3$ is sulfur; L$^3$ is n-propyl; Q$^3$ is 4-morpholinyl; and Q$^1$ is methyl; also known as, (4-Chlorophenyl)-[3-methyl-2-(3-morpholin-4-yl-propylsulfanyl)-3H-imidazol-4-yl]-methanone; M calc=379; M+H found=380;

M is —C(═O)R$^M$; R$^M$ is p-bromophenyl; A$^3$ is sulfur; L$^3$ is n-propyl; Q$^3$ is cyclohexylamino; and Q$^1$ is methyl; also known as, (4-Bromophenyl)-[2-(3-cyclohexylamino-propylsulfanyl)-3-methyl-3H-imidazol-4-yl]-methanone; M calc=435; M+H found=436;

M is —C(═O)R$^M$; R$^M$ is p-bromophenyl; A$^3$ is sulfur; L$^3$ is n-propyl; Q$^3$ is benzylamino; and Q$^1$ is methyl; also known as, [2-(3-Benzylamino-propylsulfanyl)-3-methyl-3H-imidazol-4-yl]-(4-bromo-phenyl)-methanone; M calc=443; M+H found=444;

M is —C(═O)R$^M$; R$^M$ is p-bromophenyl; A$^3$ is sulfur; L$^3$ is n-propyl; Q$^3$ is 4-thiomorpholinyl; and Q$^1$ is methyl; also known as, (4-Bromophenyl)-[3-methyl-2-(3-thiomorpholin-4-yl-propylsulfanyl)-3H-imidazol-4-yl]-methanone; M calc=439; M+H found=440;

M is —C(═O)R$^M$; R$^M$ is p-chlorophenyl; A$^3$ is sulfur; L$^3$ is n-propyl; Q$^3$ is 1-piperidyl; and Q$^1$ is methyl; also known as, (4-Chlorophenyl)-[3-methyl-2-(3-piperidin-1-yl-propyl-sulfanyl)-3H-imidazol-4-yl]-methanone; M calc=377; M+H found=378; $^1$H NMR (400 MHz, CDCl$_3$): δ 7.69 (dd, J=9.0, 2.3 Hz, 2H), 7.43 (s, 1H), 7.39 (dd, J=9.0, 2.3 Hz, 2H), 3.82 (s, 3H), 3.25 (t, J=7.1 Hz, 2H), 2.41 (br m, 4H), 1.95 (br m, 2H), 1.55 (br m, 4H), 1.36 (br m, 2H); and Example III Preparation of (4-Bromophenyl)-[3-methyl-2-(3-piperidin-1-yl-propylsulfanyl)-3H-imidazol-4-yl methanone

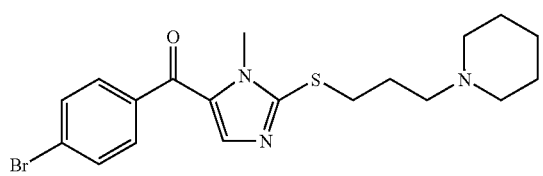

This example demonstrates the preparation of a compound of Formula I following Scheme I, wherein M is —C(═O)R$^M$; R$^M$ is p-bromophenyl; A$^3$ is sulfur; L$^3$ is n-propyl; Q$^3$ is 1-piperidyl; and Q$^1$ is methyl.

Step A: Preparation of (4-Bromophenyl)-(2-mercapto-3-3-methyl-3H-imidazol-4-yl)-methanol

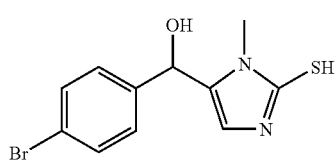

The preparation of Example I, Step A was performed employing 2-Mercapto-1-methylimidazole (5.0 g) and 4-bromobenzaldehyde (9.7 g) to provide the above identified compound as a white solid (3.0 g, 23%). M calc=298; M+H found=299.

Step B: (4-Bromophenyl)-[2-(3-chloro-propylsulfanyl)-3-methyl-3H-imidazol-4-yl]-methanol

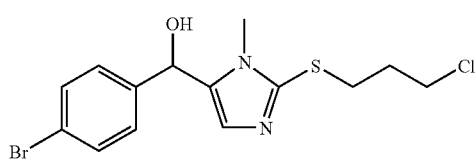

The product from Example III, Step A (3.0 g) was subjected to the same conditions as described in Example II, Step A employing 1-bromo-3-chloropropane (3.1 g) to provide the title compound (2.9 g, 77%) as a colorless oil. M calc=374; M+H found=375.

Step C: (4-Bromophenyl)-[3-methyl-2-(3-piperidin-1-yl-propylsulfanyl)-3H-imidazol-4-yl]-methanol

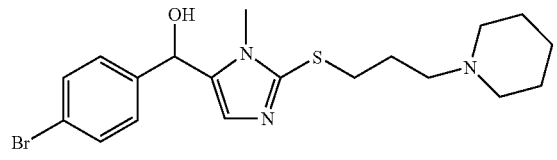

The product of Example III, Step B (0.11 g) in acetone (5 mL) and N,N-dimethylformamide (5 mL) was treated with piperidine (0.22 g) and potassium carbonate (1.8 g). The reaction mixture was allowed to stir for 16 h and then partitioned between ethyl acetate (75 mL) and aqueous saturated sodium bicarbonate solution (50 mL). The organic portion was washed with brine (50 mL), dried over magnesium sulfate, filtered and concentrated under reduced pressure. The residue was purified by column chromatography on silica gel using 2-5% methanol/dichloromethane as the eluent to provide the title compound (0.27 g, 55%). M calc=423; M+H found=424.

Step D: (4-Bromophenyl)-[3-methyl-2-(3-piperidin-1-yl-propylsulfanyl)-3H-imidazol-4-yl]-methanone The product from Example III, Step C (0.05 g) was subjected to the same conditions described in Example I, Step C ($MnO_2$, 0.05 g) to provide the title compound (0.01 g, 20%). M calc=421; M+H found=422. $^1$H NMR (400 MHz, $CDCl_3$): δ 7.65 (dd, J=8.6, 2.0 Hz, 2H), 7.55 (dd, J=8.6, 2.0 Hz, 2H), 7.46 (s, 1H), 3.86 (s, 3H), 3.28 (t, J=7.1 Hz, 2H), 2.36 (tm, J=7.0 Hz, 6H), 1.91 (m, 2H), 1.55 (m, 4H), 1.40 (br m, 2H). The compound demonstrated useful biological activity when assessed with a [$^3$H]-N-methylhistamine binding assay (see Table in Example XVIII).

Step E: Additional Compounds Prepared Following Scheme I, and Example III, Steps A, B, C, and D.

The following compounds of Formula I were prepared following Scheme I and Example III, Steps A, B, C, and D; and substituting reagents, and adjusting reaction conditions as needed. The compounds were found to have useful biological activity based on the $K_i$ (nM) value from a [3H]-N-methylhistamine binding assay.

The compounds of Formula I, wherein:

M is —CHOHR$^M$; A$^M$ is hydroxy; R$^M$ is p-chlorophenyl; A$^3$ is sulfur; L$^3$ is absent; Q$^3$ is 3-chloropropyl; and Q$^1$ is methyl; also known as, (4-Chlorophenyl)-[2-(3-chloro-propylsulfanyl)-3-methyl-3H-imidazol-4-yl]-methanol; M calc=330; M+H found=331;

M is —C(=O)R$^M$; R$^M$ is p-bromophenyl; A$^3$ is sulfur; L$^3$ is n-propyl; Q$^3$ is dimethylamino; and Q$^1$ is methyl; also known as, (4-Bromophenyl)-[2-(3-dimethylamino-propylsulfanyl)-3-methyl-3H-imidazol-4-yl]-methanone; M calc=381; M+H found=382; $^1$H NMR (400 MHz, CDCl$_3$): δ 7.63 (dd, J=25.8, 8.7 Hz, 4H), 7.42 (s, 1H), 3.82 (s, 3H), 3.25 (t, J=14.3 Hz, 2H), 2.43 (t, J=17.1 Hz, 2H), 2.24 (s, 6H), 1.91 (m, 2H);

M is —C(=O)R$^M$; R$^M$ is p-chlorophenyl; A$^3$ is sulfur; L$^3$ is n-propyl; Q$^3$ is 1-(3,4-didehydropiperidyl); and Q$^1$ is methyl; also known as, (4-Chloro-phenyl)-{2-[3-(3,4-didehydropiperidin-1-yl)-propylsulfanyl]-3-methyl-3H-imidazol-4-yl}-methanone; M calc=375; M+H found=376; $^1$H NMR (400 MHz, CDCl$_3$): δ 7.63 (d, J=8.1 Hz, 2H), 7.5 (d, J=8.1 Hz, 2H), 6.19 (s, 1H), 5.67 (s, 1H), 4.22 (s, 7H), 3.50 (s, 3H);

M is —C(=O)R$^M$; R$^M$ is p-chlorophenyl; A$^3$ is sulfur; L$^3$ is n-propyl; Q$^3$ is 4-thiomorpholinyl; and Q$^1$ is methyl; also known as, (4-chloro-phenyl)-[3-methyl-2-(3-thiomorpholin-4-yl-propylsulfanyl)-3H-imidazol-4-yl]-methanone; M calc=395; M+H found=396;

M is —C(=O)R$^M$; R$^M$ is p-chlorophenyl; A$^3$ is sulfur; L$^3$ is n-propyl; Q$^3$ is 1-[1,4']Bipiperidyl; and Q$^1$ is methyl; also known as, [2-(3-[1,4']Bipiperidinyl-1'-yl-propylsulfanyl)-3-methyl-3H-imidazol-4-yl]-(4-chloro-phenyl)-methanone; M calc=460; M+H found=461; and M is —C(=O)R$^M$; R$^M$ is p-bromphenyl; A$^3$ is sulfur; L$^3$ is absent; Q$^3$ is 3-chloropropyl; and Q$^1$ is methyl; also known as, (4-Bromophenyl)-[2-(3-chloro-propylsulfanyl)-3-methyl-3H-imidazol-4-yl]-methanone; M calc=372; M+H found=373.

Example IV

Preparation of (4-Chloro-phenyl)-{3-methyl-2-[2-(1-methyl-pyrrolidin-2-yl)-ethylsulfanyl]-3H-imidazol-4-yl}-methanone

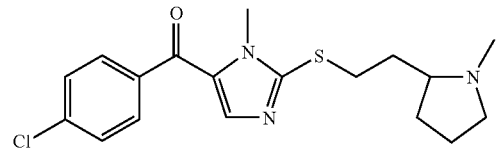

This example teaches the preparation of a compound of Formula I following Scheme II, wherein M is —C(=O)R$^M$; R$^M$ is p-chlorophenyl; A$^3$ is sulfur; L$^3$ is ethyl; Q$^3$ is 2-(1-methyl-pyrrolidyl); and Q$^1$ is methyl.

Step A: (4-Chlorophenyl)-(2-mercapto-3-methyl-3H-imidazol-4-yl)-methanone

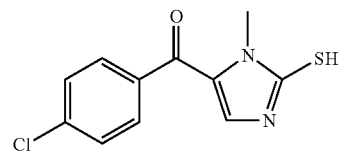

To a −5° C. solution of monomethylamine (186 g, 6 mol) in 2 L of diethyl ether was added a solution of p-chlorophenacylbromide (466 g, 2 mol) in 6 L of diethyl ether. The temperature was maintained at 0° C. during the addition and stirring was continued for 2 h. The ether and excess amine were distilled in vacuo leaving a slurry (3 L). The slurry was added to cold formyl acetic anhydride, which was prepared by heating a solution of acetic anhydride (816 mL) and formic acid (98%, 354 mL). The mixture was stored in the refrigerator overnight. The solids were then filtered and extracted with benzene. The ether was distilled in vacuo and the residue was dissolved in benzene and washed thoroughly with water and brine. The solution was dried over magnesium sulfate and charcoal. After filtration and evaporation of the solvent, the oil was dissolved in diethyl ether and seeded. The product precipitated and was filtered, and washed with diethyl ether to produce adduct 8 (155 g). This compound was carried on without further purification.

To a solution of dry benzene (25 mL) was added NaH (54.4%, 1.06 g), followed by absolute ethanol (1.15 g). After H$_2$ evolution ceased, ethyl formate (5.92 g) was added followed by adduct 8 (4.23 g). The mixture was allowed to stir for 72 h. The solvent was then evaporated and the residue was treated with water and benzene/diethyl ether (1:1). The aqueous layer was acidified and the organic layer was extracted with 1 N sodium hydroxide twice. The combined aqueous extracts were acidified, ethanol (95%) was added with warming until the solution was homogeneous. Potassium thiocyanate (4.0 g) was added and after 2.5 h of heating on a steam bath, the crystals were collected to provide imidazole 9 (0.7 g) (4-Chlorophenyl)-(2-mercapto-3-methyl-3H-imidazol-4-yl)-methanone. M calc=252; M+H found=253.

Step B: Preparation of (4-Chlorophenyl)-[3-methyl-2-[2-(1-methylpyrrolidin-2-yl)-ethylsulfanyl]-3H-imidazol-4-yl]-methanone The product from Example IV, Step A (0.15 g) was subjected to the same conditions as described in Example II, Step C, using 2-(2-chloroethyl-1-methyl-pyrrolidine hydrochloride (0.16 g) to provide (4-Chlorophenyl)-{3-methyl-2-[2-(1-methylpyrrolidin-2-yl)-ethylsulfanyl]-3H-imidazol-4-yl}-methanone (0.025 g, 11%). M calc=363; M+H found 364. $^1$H NMR (400 MHz, CDCl$_3$): δ 7.68 (dd, J=8.9, 2.2 Hz, 2H), 7.43 (s, 1H), 7.38 (dd, J=9.0, 2.3 Hz, 2H), 3.82 (s, 3H), 3.28 (m, 1H), 3.15 (m, 1H), 3.04 (m, 1H), 2.28 (s, 3H), 2.15 (br m, 1H), 2.05 (br m, 1H), 1.95 (br m, 1H), 1.65 (br m, 3H), 1.48 (br m, 1H). The compound demonstrated useful biological activity when assessed with a [$^3$H]-N-methylhistamine binding assay (see Table in Example XVIII).

Step C: Additional Compounds Prepared Following Scheme II, and Example IV, Steps A, and B.

The following compounds of Formula I were prepared following Scheme II and Example IV, Steps A and B; and substituting reagents, and adjusting reaction conditions as needed. The compounds were found to have useful biological activity based on the K$_i$ (nM) value from a [$^3$H]-N-methylhistamine binding assay.

The compounds of Formula I, wherein:

M is —C(═O)R$^M$; R$^M$ is p-chlorophenyl; A$^3$ is sulfur; L$^3$ is 2-methylpropyl; Q$^3$ is dimethylamino; and Q$^1$ is methyl; also known as, (4-Chloro-phenyl)-[2-(3-dimethylamino-2-methyl-propylsulfanyl)-3-methyl-3H-imidazol-4-yl]-methanone; M calc=351; M+H found=352; $^1$H NMR (400 MHz, CDCl$_3$): δ 7.69 (dd, J=9.1, 2.5 Hz, 2H), 7.42 (s, 1H), 7.39 (dd, J=9.1, 2.3 Hz, 2H), 3.84 (s, 3H), 3.46 (dd, J=12.9, 5.3 Hz, 1H), 3.05 (m, 1H), 2.20 (brm, 9H), 1.0 (d, J=7.1 Hz, 3H);

M is —C(═O)R$^M$; R$^M$ is p-chlorophenyl; A$^3$ is sulfur; L$^3$ is absent; Q$^3$ is 4-(1-methyl-piperidyl); and Q$^1$ is methyl; also known as, (4-Chloro-phenyl)-[3-methyl-2-(1-methyl-piperidin-4-ylsulfanyl)-3H-imidazol-4-yl]-methanone; M calc=349; M+H found=350; $^1$H NMR (400 MHz, CDCl$_3$): δ 7.72 (dd, J=8.9, 2.3 Hz, 2H), 7.47 (s, 1H), 7.41 (dd, J=9.0, 2.3 Hz, 2H), 3.86 (s, 3H), 3.75 (br s, 1H), 2.77 (brm, 2H), 2.28 (s, 3H), 2.15 (brm, 2H), 1.90 (brm, 2H);

M is —C(═O)R$^M$; R$^M$ is p-chlorophenyl; A$^3$ is sulfur; L$^3$ is n-propyl; Q$^3$ is 1-(4-methyl-piperazyl); and Q$^1$ is methyl; also known as, (4-Chloro-phenyl)-{3-methyl-2-[3-(4-methyl-piperazin-1-yl)-propylsulfanyl]-3H-imidazol-4-yl}-methanone; M calc=392; M+H found 393; $^1$H NMR (400 MHz, CDCl$_3$): δ 7.77-7.72 (dm, J=8.5 Hz, 2H), 7.47 (s, 1H), 7.46-7.42 (dm, J=8.5 Hz, 2H), 3.87 (s, 3H), 3.30 (t, J=7.1 Hz, 2H), 2.63-2.32 (m, 8H), 2.28 (s, 3H), 1.97-1.89 (m, 2H); and M is —C(═O)R$^M$; R$^M$ is phenyl; A$^3$ is sulfur; L$^3$ is n-propyl; Q$^3$ is dimethylamino; and Q$^1$ is methyl; also known as, [2-(3-Dimethylamino-propylsulfanyl)-3-methyl-3H-imidazol-4-yl]-phenyl-methanone; M calc=303; M+H found=304; $^1$H NMR (400 MHz, CDCl$_3$): δ 7.63 (d, J=7.7 Hz, 2H), 7.41 (m, 1H), 7.30 (m, 3H), 3.73 (s, 3H), 3.15 (t, J=7.14 Hz, 2H), 2.1 (br m, 6H) 1.85 (br m, 2H), 1.1 (br m, 2H).

Example V

Preparation of (4-Chlorophenyl)-[2-(1-isopropylpiperidin-4-yl-methoxy)-3-methyl-3H-imidazol-4-yl]-methanone

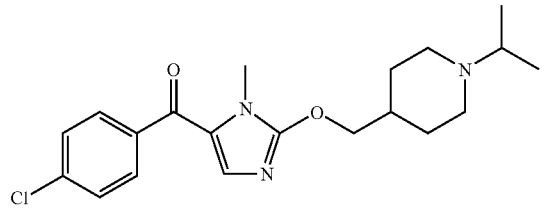

This example teaches the preparation of a compound of Formula I following Scheme III, wherein M is —C(═O)R$^M$; R$^M$ is p-chlorophenyl; A$^3$ is oxygen; L$^3$ is methyl, Q$^3$ is 4-(1-isopropyl-piperidyl); and Q$^1$ is methyl.

Step A: Preparation of (4-Chlorophenyl)-(3-methyl-2-propyisulfanyl-3H-imidazol-4-yl)-methanol

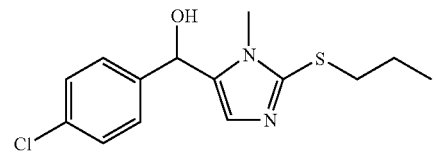

The product of Example I, Step A (3.35 g) was subjected to the same conditions as described in Example I, Step B except that bromopropane (1.4 mL) was employed as the alkylating agent to provide (4-Chlorophenyl)-(3-methyl-2-propylsulfanyl-3H-imidazol-4-yl)-methanol (2.69 g, 71%). M calc=296; M+H found=297. Calculated for C$_{14}$H$_{17}$N$_2$OSCl: C, 56.65; H, 5.77, 9.44; found C, 55.88; H, 5.88; N, 9.84.

Step B: Preparation of (4-Chlorophenyl)-(3-methyl-2-propylsulfanyl-3H-imidazol-4-yl)-methanone

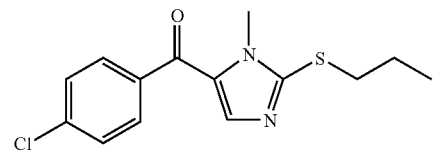

The product of Example V, Step A (2.69 g) was subjected to the same conditions as described in Example I, Step C (MnO$_2$, 3.39 g) to provide (4-Chlorophenyl)-(3-methyl-2-propylsulfanyl-3H-imidazol-4-yl)-methanone (2.67 g, 85%). M calc=294; M+H found=295. Calculated for C$_{14}$H$_{15}$N$_2$OSCl: C, 57.04; H, 5.13, 9.50; found C, 57.23; H, 4.99; N, 9.43.

Step C: Preparation of (4-Chlorophenyl)-[3-methyl-2-(propane-1-sulfonyl)-3H-imidazol-4-yl]-methanone

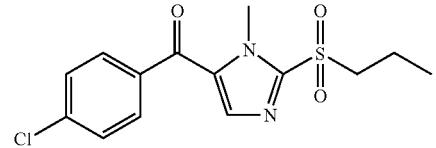

The product of Example V, Step B (2.26 g) in dichloromethane (300 mL) at 0° C. was treated with 3-chloroperoxybenzoic acid, 57% (2.58 g). After 2 h, the reaction mixture was warmed to room temperature. After stirring overnight, additional 3-chloroperoxybenzoic acid, 57% (1.6 g) was added. After 4 h, the reaction mixture was partitioned between dichloromethane and aqueous saturated sodium bicarbonate solution. The organic portion was separated, washed three times with aqueous saturated sodium bicarbonate solution, dried over sodium sulfate, filtered and evaporated to provide (4-Chloro-phenyl)-[3-methyl-2-(propane-1-sulfonyl)-3H-imidazol-4-yl]-methanone (2.3 g, 93%). M calc=326; M+H found=327. Calculated for $C_{14}H_{15}N_2O_3SCl$: C, 51.45; H, 4.63; N, 8.57; found C, 51.73; H, 4.55; N, 8.56. $^1$H NMR (400 MHz, CDCl$_3$): δ7.98 (d, 2H), 7.68 (d, 2H), 7.44 (s, 1H), 4.46 (s, 3H), 3.76-3.70 (m, 2H), 1.95-1.83 (m, 2H), 1.29 (t, 3H).

Step D: Preparation of (4-Chlorolhenyl)-[2-(1-isopropyl-piperidin-4-ylmethoxy)-3-methyl-3H-imidazol-4-yl]-methanone (1-Isopropyl-piperidin-4-yl)-methanol (0.08 g) in THF (10 mL) was treated with NaH (60% in mineral oil, 0.02 g). After 30 min, the reaction mixture was cooled to 0° C. and the product of Example V, Step C (0.125 g) in THF (5 mL) was added. After stirring overnight, the reaction mixture was partitioned between brine and ethyl acetate. The organic portion was separated, washed twice with brine, dried over sodium sulfate, filtered and concentrated. The residue was purified by column chromatography with silica gel using a gradient elution of 1-4% methanol in dichloromethane to provide (4-Chloro-phenyl)-[2-(1-isopropyl-piperidin-4-yl-methoxy)-3-methyl-3H-imidazol-4-yl]-methanone (0.07, 51%) as a white solid. M calc=375; M+H found=376. $^1$H NMR (400 MHz, CDCl$_3$): δ 7.66 (d, J=8.3 Hz, 2H), 7.37 (d, J=8.6 Hz, 2H), 7.13 (s, 1H), 4.24 (d, J=6.1 Hz, 2H), 3.69 (s, 3H), 2.88 (br d, J=11.0 Hz, 2H), 2.69 (m, 1H), 2.12 (br dd, J=12.6, 9.6 Hz, 2H), 1.88-1.69 (br m, 1H), 1.37 (br dd (J=23.2, 9.3 Hz, 2H), 0.99 (d, J=6.6 Hz, 6H). The compound demonstrated useful biological activity when assessed with a [$^3$H]-N-methylhistamine binding assay (see Table in Example XVIII).

Step E: Additional Compounds Prepared Following Scheme III, and Example V, Steps A, B, C, and D.

The following compounds of Formula I were prepared following Scheme III and Example V, Steps A, B, C, and D; and substituting reagents, and adjusting reaction conditions as needed. The compounds were found to have useful biological activity based on the $K_i$ (nM) value from a [$^3$H]-N-methylhistamine binding assay.

The compounds of Formula I, wherein:

M is —C(=O)R$^M$; R$^M$ is p-chlorophenyl; A$^3$ is sulfoxide (S=O); L$^3$ is absent; Q$^3$ is methyl; and Q$^1$ is methyl; also known as, (4-Chloro-phenyl)-(2-methanesulfinyl-3-methyl-3H-imidazol-4-yl)-methanone; M calc=282; M+H found=283;

M is —C(=O)R$^M$; R$^M$ is p-chlorophenyl; A$^3$ is oxygen; L$^3$ is ethyl; Q$^3$ is 1-piperidyl; and Q$^1$ is methyl; also known as, (4-Chlorophenyl)-[3-methyl-2-(2-piperidin-1-yl-ethoxy)-3H-imidazol-4-yl]-methanone; M calc=347; M+H found=348; $^1$H NMR (400 MHz, CDCl$_3$): δ 7.67 (dm, J=8.6 Hz, 2H), 7.37 (dm, J=8.6 Hz, 2H), 7.14 (s, 1H), 4.52 (t, J=5.8 Hz, 2H), 3.69 (s, 3H), 2.74 (t, J=5.8 Hz, 2H), 2.49-2.40 (m, 4H), 1.57-1.48 (m, 4H), 1.42-1.32 (m, 2H);

M is —C(=O)R$^M$; R$^M$ is p-chlorophenyl; A$^3$ is oxygen; L$^3$ is n-propyl; Q$^3$ is 1-piperidyl; and Q$^1$ is methyl; also known as, (4-Chlorophenyl)-[3-methyl-2-(3-piperidin-1-yl-propoxy)-3H-imidazol-4-yl]-methanone; M calc=361; M+H found=362; $^1$H NMR (400 MHz, CDCl$_3$): δ 7.67 (d, J=8.6 Hz, 2H), 7.38 (d, J=8.6 Hz, 2H), 7.14 (s, 1H), 4.44 (t, J=7.0 Hz, 2H), 3.67 (s, 3H), 2.40 (t, J=7.3 Hz, 2H), 2.37-2.29 (br m, 2H), 2.00-1.91 (m, 2H), 1.57-1.48 (m, 4H), 1.41-1.33 (m, 2H);

M is —C(=O)R$^M$; R$^M$ is p-chlorophenyl; A$^3$ is NH; L$^3$ is n-propyl; Q$^3$ is 1-piperidyl; and Q$^1$ is methyl; also known as, (4-Chlorophenyl)-[3-methyl-2-(3-piperidin-1-yl-propylamino)-3H-imidazol-4-yl]-methanone; $^1$H NMR (400 MHz, CDCl$_3$): δ 7.75 (d, J=8.3 Hz, 2H), 7.46 (d, J=8.1 Hz, 2H), 7.21 (s, 1H), 4.51 (t, J=6.3 Hz, 2H), 3.76 (s, 3H), 2.47-2.32 (tm, J=6.8 Hz, 6H), 2.10-1.95 (m, 2H), 1.66-1.53 (m, 4H), 1.49-1.37 (m, 2H);

M is —C(=O)R$^M$; R$^M$ is p-bromophenyl; A$^3$ is oxygen; L$^3$ is n-propyl; Q$^3$ is 1-piperidyl; and Q$^1$ is methyl; also known as, (4-Bromophenyl)-[3-methyl-2-(3-piperidin-1-yl-propoxy)-3H-imidazol-4-yl]-methanone; M calc=405; M+H found=406;

M is —C(=O)R$^M$; R$^M$ is p-bromophenyl; A$^3$ is oxygen; L$^3$ is absent; Q$^3$ is 4-(1-isopropyl-piperidyl); and Q$^1$ is methyl; also known as, (4-Bromo-phenyl)-[2-(1-isopropyl-piperidin-4-yloxy)-3-methyl-3H-imidazol-4-yl]-methanone; M calc=405; M+H found=406; $^1$H NMR (400 MHz, CDCl$_3$): δ 7.60 (dd, J=8.3, 2.0 Hz, 2H), 7.54 (dd, J=8.6, 2.0 Hz, 2H), 7.14 (s, 1H), 4.93 (m, 1H), 3.68 (s, 3H), 2.78-2.62 (m, 3H), 2.38 (br t, J=8.6 Hz, 2H), 2.13-1.99 (m, 2H), 1.88-1.75 (m, 2H), 0.99 (d, J=6.6 Hz, 6H);

M is —C(=O)R$^M$; R$^M$ is p-bromophenyl; A$^3$ is oxygen; L$^3$ is methyl; Q$^3$ is 4-(1-isopropyl-piperidyl); and Q$^1$ is methyl; also known as, (4-Bromophenyl)-[2-(1-isopropyl-piperidin-4-ylmethoxy)-3-methyl-3H-imidazol-4-yl]-methanone; M calc=419; M+H found=420; $^1$H NMR (400 MHz, CDCl$_3$): δ 7.59 (dd, J=8.1, 2.0 Hz, 2H), 7.54 (dd, J=8.6, 1.8 Hz, 2H), 7.13 (s, 1H), 4.24 (d, J=6.0 Hz, 2H), 3.68 (s, 3H), 2.88 (br d, J=11.9 Hz, 2H), 2.74-2.62 (m, 1H), 2.11 (td, J=11.9, 2.5 Hz, 2H), 1.85-1.71 (br m, 3H), 1.37 (br dd, J=12.4, 3.5 Hz, 2H), 0.99 (d, J=6.8 Hz, 6H);

M is —C(=O)R$^M$; R$^M$ is p-chlorophenyl; A$^3$ is oxygen; L$^3$ is n-propyl; Q$^3$ is dimethylamino; and Q$^1$ is methyl; also known as, (4-Chlorophenyl)-[2-(3-dimethylamino-propoxy)-3-methyl-3H-imidazol-4-yl]-methanone; M calc=321; M+H found=322; $^1$H NMR (400 MHz, CD$_3$OD): δ 7.78-7.72 (dm, J=8.4 Hz, 2H), 7.48-7.43 (dm, J=6.7 Hz, 2H), 7.22 (s, 1H), 4.53 (t, J=6.2 Hz, 2H), 3.75 (s, 3H), 2.46 (t, J=7.1 Hz, 2H), 2.27 (s, 6H), 2.08-1.73 (m, 2H);

M is —C(=O)R$^M$; R$^M$ is p-bromophenyl; A$^3$ is oxygen; L$^3$ is methyl; Q$^3$ is 1-tert-butoxycarbonyl-piperidin-4-yl; and Q$^1$ is methyl; also known as, 4-[5[((4-bromobenzoyl)-1-methyl-1H-imidazol-2-yloxymethyl]-piperidine-1-carboxylic acid tert-butyl ester; M calc=477; M+H found=478;

M is —C(=O)R$^M$; R$^M$ is p-bromophenyl; A$^3$ is oxygen; L$^3$ is ethyl; Q$^3$ is 1-(4-isopropylpiperazyl); and Q$^1$ is methyl; also known as, (4-Bromophenyl)-{2-[2-(4-isopropyl-piperazin-1-yl)-ethoxy]-3-methyl-3H-imidazol-4-yl}-methanone; M calc=434; M+H found=435; $^1$H NMR (400 MHz, CDCl$_3$): δ 7.62-7.57 (dm, J=8.4 Hz, 2H), 7.57-7.52 (dm, J=8.3 Hz, 2H), 7.14 (s, 1H), 4.52 (t, J=5.7 Hz, 2H), 3.68 (s, 3H), 2.77 (t, J=5.7 Hz, 2H), 2.64-2.40 (m, 8H), 1.85 (br s, 1H), 0.98 (d, J=6.5 Hz, 6H);

M is —C(=O)R$^M$; R$^M$ is phenyl; A$^3$ is oxygen; L$^3$ is n-propyl; Q$^3$ is 1-piperidyl; and Q$^1$ is methyl; also known as, [3-Methyl-2-(3-piperidin-1-yl-propoxy)-3H-imidazol-4-yl]-phenyl-methanone; M calc=327; M+H found=328; and M is —C(=O)R$^M$; R$^M$ is p-bromophenyl; A$^3$ is oxygen; L$^3$ is ethan-1-yl-2-ylidene; Q$^3$ is 4-(1-isopropyl-piperidyl); and Q$^1$ is methyl; also known as, (4-Bromophenyl)-{2-[2-(1-isopropyl-piperidin-4-ylidene)-ethoxy]-3-methyl-3H- imidazol-4-yl}-methanone; $^1$H NMR (400 MHz, CDCl$_3$): δ 7.57 (dd, J=22.4, 8.4 Hz, 4H), 7.14 (s, 1H), 5.43 (t, J=7.2 Hz, 1H), 4.90 (d, J=7.1 Hz, 1H), 3.68 (s, 3H), 2.74-2.65 (m, 1H), 2.46 (ddd, J=11.2, 5.5, 5.5 Hz, 4H), 2.32 (t, J=5.5 Hz, 2H), 2.23 (t, J=5.5 Hz, 2H), 0.97 (d, J=6.6 Hz, 6H).

Step F: Additional Compounds That Can Be Prepared Following Scheme III and Example V, Steps A, B, C, and D, and E.

The following compound of Formula I was prepared by first following Scheme III and Example V, Steps A, B, C, D, and E to prepare 4-[5[(4-bromobenzoyl)-1-methyl-1H-imidazol-2-yloxymethyl]-piperidine-1-carboxylic acid tert-butyl ester (see Step E above). This intermediate was then treated with trifluoroacetic acid in dichloromethane under standard tert-butoxycarbonyl removal conditions to yield the compound of Formula I wherein:

M is —C(=O)R$^M$; R$^M$ is p-bromophenyl; A$^3$ is oxygen; L$^3$ is methyl; Q$^3$ is 4-piperidyl; and Q$^1$ is methyl; also known as, (4-Bromophenyl)-[3-methyl-2-(piperidin-4-ylmethoxy)-3H-imidazol-4-yl]-methanone; $^1$H NMR (400 MHz, CDCl$_3$/CD$_3$OD (~1:1)): δ 7.57 (m, 4H), 7.13 (s, 1H), 4.27 (d, 2H), 3.69 (s, 3H), 3.40 (m, 2H), 2.86 (m, 2H), 2.10 (br s, 1H), 1.96 (m, 2H), 1.59 (m, 2H).

Step G: Additional Compounds That Can Be Prepared Following Scheme III and Example V, Steps A, B, C, D, E and F.

The following compounds of Formula I were prepared by first following Scheme III and Example V, Steps A, B, C, D, E, and F to prepare (4-Bromophenyl)-[3-methyl-2-(piperidin-4-ylmethoxy)-3H-imidazol-4-yl]-methanone (see Step F above). This intermediate was then subjected to the reductive amination procedure outlined in Example XV, using the appropriate aldehydes to yield the compounds of Formula I wherein:

M is —C(=O)R$^M$; R$^M$ is p-bromophenyl; A$^3$ is oxygen; L$^3$ is ethyl; Q$^3$ is 4-(1-isopropylpiperidyl); and Q$^1$ is methyl; also known as, (4-Bromophenyl)-{2-[2-(1-isopropyl-piperidin-4-yl)-ethoxy]-3-methyl-3H-imidazol-4-yl}-methanone; M calc=433; M+H found=434; $^1$H, (500 MHz, CDCl$_3$): δ 7.62-7.57 (dm, J=8.5 Hz, 2H), 7.56-7.53 (dm, J=8.5 Hz, 2H), 7.12 (s, 1H), 4.44 (t, J=6.6 Hz, 2H), 3.68 (s, 3H), 3.12-2.72 (m, 3H), 2.36-2.10 (m, 2H), 1.88-1.64 (m, 3H), 1.18-0.97 (m, 6H);

M is —C(=O)R$^M$; R$^M$ is p-bromophenyl; A$^3$ is oxygen; L$^3$ is methyl; Q$^3$ is 4-(1-ethyl-piperidyl); and Q$^1$ is methyl; also known as, (4-Bromophenyl)-[2-(1-ethyl-piperidin-4-ylmethoxy)-3-methyl-3H-imidazol-4-yl]-methanone; $^1$H NMR (400 MHz, CDCl$_3$): δ 7.35 (s, 4H), 6.69 (s, 1H), 5.83 (s, 1H), 3.49 (s, 3H), 3.08 (m, 2H), 1.65 (m, 3H), 1.53 (m, 2H), 1.27 (m, 3H), 0.86 (d, J=6.6 Hz, 6H);

M is —C(=O)R$^M$; R$^M$ is p-bromophenyl; A$^3$ is oxygen; L$^3$ is methyl; Q$^3$ is 4-(1-sec-butyl-piperidyl); and Q$^1$ is methyl; also known as, (4-Bromophenyl)-[2-(1-sec-butyl-piperidin-4-ylmethoxy)-3-methyl-3H-imidazol-4-yl]-methanone; $^1$H NMR (400 MHz, CDCl$_3$): δ 7.70 (dd, J=8.3, 2.3 Hz, 2H), 7.65 (dd, J=8.6, 2.0 Hz, 2H), 7.30 (s, 1H), 4.35 (d, J=6.3 Hz, 2H), 3.8 (s, 3H), 2.9 (br m, 1H), 2.85 (br m, 2H), 0.9 (m, 3H), 0.8 (m, 3H);

M is —C(=O)R$^M$; R$^M$ is p-bromophenyl; A$^3$ is oxygen; L$^3$ is methyl; Q$^3$ is 4-(1-methyl-piperidyl); and Q$^1$ is methyl; also known as, (4-Bromophenyl)-[3-methyl-2-(1-methyl-piperidin-4-ylmethoxy)-3H-imidazol-4-yl]-methanone; $^1$H NMR (400 MHz, CDCl$_3$): δ 7.58 (dd, J=20.9, 8.8 Hz, 4H), 7.14 (s, 1H), 4.26 (d, J=6.1 Hz, 2H), 3.69 (s, 3H), 2.85 (d, J=11.4 Hz, 2H), 1.58 (br s, 5H), 1.40 (m, 3H);

M is —C(=O)R$^M$; R$^M$ is p-bromophenyl; A$^3$ is oxygen; L$^3$ is methyl; Q$^3$ is 4-[1-(3-methylbutyl)-piperidyl]; and Q$^1$ is methyl; also known as, (4-Bromophenyl)-{3-methyl-2-[1-(3-methyl-butyl)-piperidin-4-ylmethoxy]-3H-imidazol-4-yl}-methanone; M calc=447; M+H found=448;

M is —C(=O)R$^M$; R$^M$ is p-bromophenyl; A$^3$ is oxygen; L$^3$ is methyl; Q$^3$ is 4-(1'-isopropyl-[1,4']bipiperidyl); and Q$^1$ is methyl; also known as, (4-Bromophenyl)-[2-(1'-isopropyl-[1,4']bipiperidinyl-4-ylmethoxy)-3-methyl-3H-imidazol-4-yl]-methanone; M calc=502; M+H found=503; and M is —C(=O)R$^M$; R$^M$ is p-bromophenyl; A$^3$ is oxygen; L$^3$ is methyl; Q$^3$ is 4-(1-cyclohexyl-piperidyl); and Q$^1$ is methyl; also known as, (4-Bromophenyl)-[2-(1-cyclohexyl-piperidin-4-ylmethoxy)-3-methyl-3H-imidazol-4-yl]-methanone; M calc=459; M+H found=460; $^1$H NMR (400 MHz, CDCl$_3$): δ 7.62-7.57 (m, 2H), 7.56-7.51 (m, 2H), 7.14-7.11 (m, 1H), 4.32-4.21 (m, 2H), 3.71-3.66 (m, 3H), 3.20-3.03 (m, 1H), 3.00-2.87 (m, 1H), 2.57-2.46 (m, 1H), 2.46-2.25 (m, 1H), 2.05-1.88 (m, 2H), 1.88-1.69 (m, 4H), 1.69-1.42 (m, 6H), 1.32-1.13 (m, 3H), 1.13-1.10 (m, 1H).

Example XI

Preparation of (4-Chlorophenyl)-[2-(1-isopropyl-piperidin-4-yloxy)-3-methyl-3H-imidazol-4-yl]-methanone

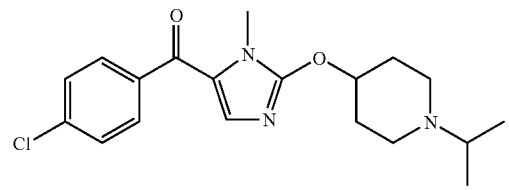

This example teaches the preparation of a compound of Formula I following Scheme IX, wherein M is —C(=O)R$^M$; R$^M$ is p-chlorophenyl; A$^3$ is oxygen; L$^3$ is absent; Q$^3$ is 1-isopropyl-piperidin-4-yl; and Q$^1$ is methyl.

Step A: Preparation of 1-Methyl-2-phenylsulfanyl-1H-imidazole

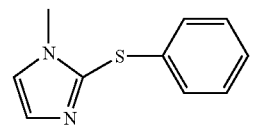

To a stirred solution of 1-Methyl-1H-imidazole (3.00 mL) in dry THF (120 mL) was added at −78° C. n-BuLi (15.0 mL, 2.50 M in hexanes). The reaction solution was stirred for 20 minutes at −78° C. and diphenyldisulfide (8.21 g) was added. The reaction mixture was stirred for 15 minutes at −78° C. and was allowed to warm to room temperature over 45 minutes. Water (25.0 mL) was added and the solvent was removed in vacuo. The residue was dissolved in dichloromethane (500 mL) and the organic layer was washed with water (2×50.0 mL). The organic layer was dried over magnesium sulfate and the solvent was removed in vacuo. The residue was purified by flash chromatography on silica gel (hexanes/acetone) to give the title compound (5.85 g).

Step B: Preparation of (4-Chlorophenyl)-(3-methyl-2-phenylsulfanyl-3H-imidazol-4-yl)-methanol

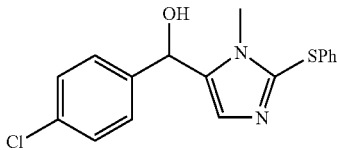

To a stirred solution of 2,2,6,6-tetramethylpiperidine (3.54 mL) in dry THF (50.0 mL) and 1,2-dimethoxyethane (DME, 20.0 mL) was added at −78° C. n-BuLi (8.00 mL, 2.50 M in hexanes). The solution was stirred for 15 minutes at −78° C. and a solution of the product of Example XI, Step A (3.81 g) in dry THF (5.00 mL) was added at −78° C. The reaction mixture was allowed to warm to room temperature and was stirred for 12 h at room temperature. Water (10.0 mL) was added and the solvent was removed in vacuo. The residue was dissolved in dichloromethane (650 mL) and the organic layer was washed with water (2×150 mL). The organic layer was dried over magnesium sulfate and the solvent was removed in vacuo. The residue was purified by flash chromatography on silica gel (hexanes/acetone) to give the title compound (4.60 g).

Step C: Preparation of (4-Chlorophenyl)-(3-methyl-2-phenylsulfanyl-3H-imidazol-4-yl)-methanone

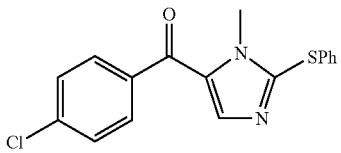

To a stirred solution of the product of Example XI, Step B (1.00 g) in dry dichloromethane (250.0 mL) was added at room temperature $MnO_2$ (3.02 g). The reaction mixture was stirred for 24 h at room temperature and was filtered through diatomaceous earth. The solvent was removed in vacuo and the residue was purified by flash chromatography (hexanes/acetone) to give the title compound (620 mg).

Step D: Preparation of (2-Benzenesulfonyl-3-methyl-3H-imidazol-4-yl)-(4-chlorophenyl)-methanone

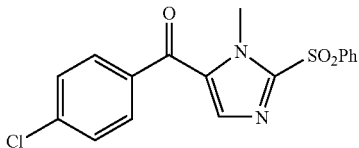

To a stirred solution of the product of Example XI, Step C (620 mg) in diethyl ether (100 mL) was added at room temperature 3-chloroperoxybenzoic acid (57%, 2.86 g). The reaction solution was stirred for 6 h at room temperature and diethyl ether (650 mL) was added. The organic layer was washed with saturated sodium bicarbonate (3×150 mL), water (150 mL) and brine (150 mL) and was dried over magnesium sulfate. The solvent was removed in vacuo and the residue was purified by flash chromatography on silica gel (hexanes/acetone) to give the material (802 mg) containing the title compound, which was used without additional purification.

Step E: Preparation of (4-Chlorophenyl)-[2-(1-isopropyl-piperidin-4-yloxy)-3-methyl-3H-imidazol-4-yl]-methanone To a stirred solution of 1-isopropyl-piperidin-4-ol (301 mg) in dry THF (10.0 mL) was added at room temperature NaH (60% dispersion in mineral oil, 76.0 mg). The reaction mixture was stirred for 30 minutes at room temperature and a solution of the product of Example XI, Step D (150 mg) in dry THF (1.00 mL) was added. The reaction mixture was stirred for 18 h at room temperature and water (1.00 mL) was added. The solvent was removed in vacuo and the residue was dissolved in dichloromethane (300 mL). The organic layer was washed with saturated sodium bicarbonate (2×50.0 mL) and water (50.0 mL) and was dried over magnesium sulfate. The solvent was removed in vacuo and the residue was purified by flash chromatography on silica gel ($CHCl_3/NH_3$, 2 M in methanol) to give the title compound (82.0 mg) M calc=361, M+H found=362; $^1H$ NMR (400 MHz, $CD_3OD$): δ 7.83-7.76 (dm, J=8.4 Hz, 2H), 7.57-7.50 (dm, J=9.0 Hz, 2H), 7.26 (s, 1H), 4.50-4.92 (m, 1H), 3.75 (s, 3H), 2.92-2.70 (m, 3H), 2.59-2.45 (m, 2H), 2.20-2.04 (m, 2H), 2.00-1.80 (m, 2H), 1.11 (d, J=6.5 Hz, 6H). The compound demonstrated useful biological activity when assessed with a [3H]-N-methylhistamine binding assay (see Table in Example XVIII).

Step F: Additional Compounds Prepared Following Scheme IX, and Example XI, Steps A, B, C, D, and E.

The following compounds of Formula I were prepared following Scheme IX and Example XI, Steps A, B, C, D, and E; and substituting reagents, and adjusting reaction conditions as needed. The compounds were found to have useful biological activity based on the $K_i(nM)$ value from a $[^3H]$-N-methylhistamine binding assay.

The compounds of Formula I, wherein:

M is $-C(=O)R^M$; $R^M$ is methyl; $A^3$ is sulfur; $L^3$ is n-propyl; $Q^3$ is dimethylamino; and $Q^1$ is methyl; also known as, 1-[2-(3-Dimethylamino-propylsulfanyl)-3-methyl-3H-imidazol-4-yl]-ethanone; M calc=241; M+H found=242; $^1H$ NMR (400 MHz, $CDCl_3$): δ 7.76 (s, 1H), 3.83 (s, 3H), 3.39 (t, J=6.4 Hz, 2H), 2.43-2.38 (m, 5H), 2.23 (s, 6H), 1.95-1.88 (m, 2H);

M is $-C(=O)R^M$; $R^M$ is p-chlorophenyl; $A^3$ is sulfur; $L^3$ is n-propyl; $Q^3$ is dimethylamino; and $Q^1$ is methyl; also known as, (4-Chlorophenyl)-[2-(3-dimethylamino-propylsulfanyl)-3-methyl-3H-imidazol-4-yl]-methanone; M calc=337; M+H found=338; $^1H$ NMR (400 MHz, $CDCl_3$): δ 7.81-7.73 (dm, J=8.5 Hz, 2H), 7.50 (s, 1H), 7.48-7.44 (dm, J=8.6 Hz, 2H), 3.91 (s, 3H), 3.33 (t, J=7.1 Hz, 2H), 2.45 (t, J=7.1 Hz, 2H), 2.27 (s, 6H), 2.0-1.91 (m, 2H);

M is $-C(=O)R^M$; $R^M$ is p-chlorophenyl; $A^3$ is oxygen; $L^3$ is absent; $Q^3$ is 4-(piperidin-1-ylmethyl)phenyl; and $Q^1$ is methyl; also known as, (4-Chlorophenyl)-[3-methyl-2-(4-piperidin-1-ylmethyl-phenoxy)-3H-imidazol-4-yl]-methanone; M calc=409; M+H found=410;

M is $-C(=O)R^M$; $R^M$ is methyl; $A^3$ is oxygen; $L^3$ is propyl; $Q^3$ is 1-piperidyl; and $Q^1$ is methyl; also known as, 1-[3-Methyl-2-(3-piperidin-1-yl-propoxy)-3H-imidazol-4-yl]-ethanone; M calc=265; M+H found=266; and M is $-C(=O)R^M$; $R^M$ is p-chlorophenyl; $A^3$ is sulfur; $L^3$ is absent; $Q^3$ is 4-(1-isopropyl-piperidyl); and $Q^1$ is methyl; also known as, (4-Chlorophenyl)-[2-(1-isopropyl-piperidin-4-ylsulfanyl)-3-methyl-3H-imidazol-4-yl]-methanone; M calc=377; M+H found=378; $^1H$ NMR (400 MHz, $CD_3OD$):

δ 7.85-7.79 (dm, J=8.4 Hz, 2H), 7.58-7.51 (m, 3H), 3.94 (s, 3H), 3.68-3.63 (m, 1H), 2.97-2.86 (m, 2H), 2.80-2.72 (m, 1H), 2.38 (t, J=10.9 Hz, 2H), 2.17-2.05 (m, 2H), 1.82-1.68 (m, 2H), 1.09 (d, J=6.6 Hz, 6H).

Step G: Additional Compounds That Can Be Prepared Following Scheme IX and Example XI, Steps A, B, C, D, and E.

The following compound of Formula I was prepared by first following Scheme IX and Example XI, Steps A, B, C, D, and E to prepare the compound wherein M is —C(=O)$R^M$; $R^M$ is p-chlorophenyl; $A^3$ is sulfur; $L^3$ is n-propyl; $Q^3$ is 2-(1,3-dioxolanyl and $Q^1$ is methyl (that is, (4-Chlorophenyl)-[2-(3-[1,3]dioxolan-2-yl-propylsulfanyl)-3-methyl-3H-imidazol-4-yl]-methanone). M calc=366; M+H found=367. The dioxolane of the intermediate was then removed under the standard mild conditions of pyridinium p-toluenesulfonate (PPTS). Subsequent reductive amination conditions as described in Example XV using piperidine as the basic component provided the compound of Formula I wherein:

M is —C(=O)$R^M$; $R^M$ is p-chlorophenyl; $A^3$ is sulfur; $L^3$ is n-butyl; $Q^3$ is 1-piperidyl; and $Q^1$ is methyl; also known as, (4-Chlorophenyl)-[3-methyl-2-(4-piperidin-1-yl-butylsulfanyl)-3H-imidazol-4-yl]-methanone; M calc=391; M+H found=392; $^1$H NMR (400 MHz, CD$_3$OD): δ 7.81 (d, J=8.4 Hz, 2H), 7.53 (d, J=8.4 Hz, 3H), 7.54 (s, 1H), 3.90 (s, 3H), 3.31-3.25 (m, 2H), 2.66-2.50 (m, 4H), 2.48-2.44 (m, 2H), 1.80-1.68 (m, 4H), 1.68-1.58 (m, 4H), 1.54-1.44 (m, 2H).

Example XII

Preparation of

[3-Methyl-2-(3-piperidin-1-yl-propoxy)-3H-imidazol-4-yl]-naphthalen-1-yl-methanone

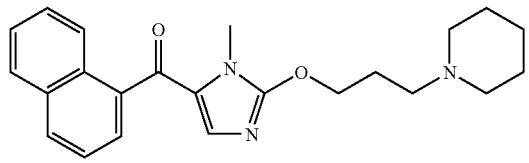

This example teaches the preparation of a compound of Formula I following Scheme X, wherein M is —C(=O)$R^M$; $R^M$ is 1-naphthalenyl; $A^3$ is oxygen; $L^3$ is propyl; $Q^3$ is 1-piperidyl; and $Q^1$ is methyl.

Step A: Preparation of 2-Benzenesulfonyl-1-methyl-1H-imidazole

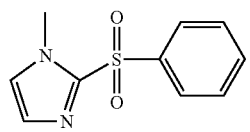

To a stirred solution of 1-methyl-2-phenylsulfanyl-1H-imidazole (the product of Step A in Example XI) (3.00 g) in diethyl ether (150 mL) was added at room temperature 3-chloroperoxybenzoic acid (57%, 22.7 g). The reaction solution was stirred for 18 h at room temperature and diethyl ether (750 mL) was added. The organic layer was washed with saturated sodium bicarbonate (3×200 mL), water (200 mL) and brine (200 mL) and was dried over magnesium sulfate. The solvent was removed in vacuo and the residue was purified by flash chromatography on silica gel (hexanes/acetone) to give the title compound (2.21 g).

Step B: Preparation of 1-[3-(1-Methyl-1H-imidazol-2-yloxy)-propyl]-piperidine

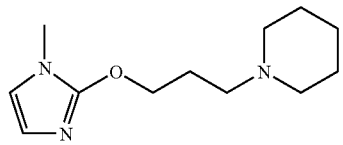

To a stirred solution of 3-piperidin-1-yl-propan-1-ol (3.19 g) in dry THF (50.0 mL) was added at room temperature NaH (60% dispersion in mineral oil, 800 mg). The reaction mixture was stirred for 30 minutes at room temperature and a solution of the product of Example XII, Step A (990 mg) in dry THF (20.0 mL) was added. The reaction mixture was heated under reflux for 20 h and was allowed to cool to room temperature. Water (10.0 mL) was added and the solvent was removed in vacuo. The residue was dissolved in dichloromethane (400 mL) and the organic layer was washed with water (2×100 mL). The organic layer was dried over magnesium sulfate and the solvent was removed in vacuo. The residue was purified by flash chromatography on silica gel (CHCl$_3$/NH$_3$, 2 M in methanol) to give 778 mg of the compound of Formula I wherein M is hydrogen; $A^3$ is oxygen; $L^3$ is n-propyl; $Q^3$ is 1-piperidyl; and $Q^1$ is methyl; also known as, 1-[3-(1-Methyl-1H-imidazol-2-yloxy)-propyl]-piperidine. M calc=223; M+H found=224.

Step C: Preparation of [3-Methyl-2-(3-piperidin-1-yl-propoxy)-3H-imidazol-4-yl]-naphthalen-1-yl-methanol

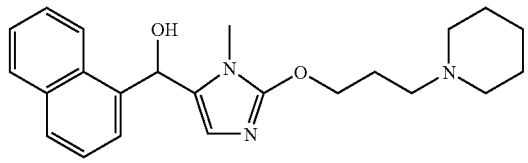

To a stirred solution of 2,2,6,6-tetramethylpiperidine (140 mg) in dry THF (5.00 mL) and 1,2-dimethoxyethane (DME, 2.50 mL) was added at −78° C. n-BuLi (467 µL, 1.92 M in hexanes). The solution was stirred for 15 minutes at −78° C. and a solution of the product of Example XII, Step B (100 mg) in dry THF (1.00 mL) was added at −78° C. The reaction mixture was stirred for 45 minutes at −78° C. and a solution of 1-naphthaldehyde (106 mg) in dry THF (1.00 mL) was added at −78° C. The reaction mixture was allowed to warm to room temperature and was stirred for 18 h at room temperature. Water (1.00 mL) was added and the solvent was removed in vacuo. The residue was dissolved in dichloromethane (20.0 mL) and the organic layer was washed with water utilizing a Varian chem elute 1005 cartridge. The organic layer was dried over magnesium sulfate and the solvent was removed in vacuo. The residue was purified by flash chromatography on silica gel (CHCl$_3$/NH$_3$, 2M in methanol) to give the material (35.0 mg) containing the title compound, which was used without additional purification.

Step D Preparation of [3-Methyl-2-(3-piperidin-1-yl-propoxy)-3H-imidazol-4-yl]-naphthalen-1-yl-methanone To a stirred solution of the product of Example XII, Step C (35.0 mg) in dry dichloromethane (5.00 mL) was added at room temperature $MnO_2$ (85%, activated, 47.0 mg). The reaction mixture was stirred for 18 h at room temperature and was filtrated over diatomaceous earth. The solvent was removed in vacuo and the residue was purified by flash chromatography ($CHCl_3/NH_3$, 2M in methanol) to give the title compound (8.00 mg). M calc=377, M+H found=378. $^1$H NMR (400 MHz, $CD_3OD$): δ 8.09-8.04 (m, 2H), 7.98-7.95 (m, 1H), 7.69-7.67 (m, 1H), 7.57-7.50 (m, 3H), 6.98 (s, 1H), 4.48 (t, J=6.3 Hz, 2H), 3.87 (s, 3H), 2.56-2.45 (m, 6H), 2.09-2.02 (m, 2H), 1.66-1.60 (m, 4H), 1.51-1.48 (m, 2H). The compound demonstrated useful biological activity when assessed with a [$^3$H]-N-methylhistamine binding assay (see Table in Example XVIII).

Step E: Additional Compounds Prepared Following Scheme X, and Example XII, Steps A, B, C, and D.

The following compounds of Formula I were prepared following Scheme X and Example XII, Steps A, B, C, and D; and substituting reagents, and adjusting reaction conditions as needed. The compounds were found to have useful biological activity based on the $K_i$(nM) value from a [$^3$H]-N-methylhistamine binding assay.

The compounds of Formula I, wherein:

M is —C(=O)$R^M$; $R^M$ is methyl; $A^3$ is oxygen; $L^3$ is propyl; $Q^3$ is 1-piperidyl; and $Q^1$ is methyl; also known as, 1-[3-Methyl-2-(3-piperidin-1-yl-propoxy)-3H-imidazol-4-yl]-ethanone; M calc=265; M+H found=266;

M is —CHOH$R^M$; $A^M$ is hydroxy; $R^M$ is methyl; $A^3$ is oxygen; $L^3$ is propyl; $Q^3$ is 1-piperidyl; and $Q^1$ is methyl; also known as, 1-[3-Methyl-2-(3-piperidin-1-yl-propoxy)-3H-imidazol-4-yl]-ethanol; M calc=267; M+H found=268; $^1$H NMR (400 MHz, $CDCl_3$): δ 6.47 (s, 1H), 4.73 (m, 1H), 4.34 (m, 2H), 3.43 (s, 3H), 2.48-2.36 (m, 6H), 2.02-1.94 (m, 2H), 1.63-1.54 (m, 7H), 1.47-1.41 (m, 2H);

M is —C(=O)$R^M$; $R^M$ is 4-methoxyphenyl; $A^3$ is oxygen; $L^3$ is n-propyl; $Q^3$ is 1-piperidyl; and $Q^1$ is methyl; also known as, (4-Methoxyphenyl)-[3-methyl-2-(3-piperidin-1-yl-propoxy)-3H-imidazol-4-yl]-methanone; M calc=357; M+H found=358;

M is —C(=O)$R^M$; $R^M$ is 4-pyridyl; $A^3$ is oxygen; $L^3$ is n-propyl; $Q^3$ is 1-piperidyl; and $Q^1$ is methyl; also known as, [3-Methyl-2-(3-piperidin-1-yl-propoxy)-3H-imidazol-4-yl]-pyridin-4-yl-methanone; M calc=328; M+H found=329;

M is —C(=O)$R^M$; $R^M$ is 3-pyridyl; $A^3$ is oxygen; $L^3$ is n-propyl; $Q^3$ is 1-piperidyl; and $Q^1$ is methyl; also known as, [3-Methyl-2-(3-piperidin-1-yl-propoxy)-3H-imidazol-4-yl]-pyridin-3-yl-methanone; M calc=328; M+H found=329;

M is —C(=O)$R^M$; $R^M$ is 2-pyridyl; $A^3$ is oxygen; $L^3$ is n-propyl; $Q^3$ is 1-piperidyl; and $Q^1$ is methyl; also known as, [3-Methyl-2-(3-piperidin-1-yl-propoxy)-3H-imidazol-4-yl]-pyridin-2-yl-methanone; M calc=328; M+H found=329; $^1$H NMR (400 MHz, $CD_3OD$): δ 8.69-8.68 (m, 1H), 8.02-7.97 (m, 3H), 7.62-7.56 (m, 1H), 4.50 (t, J=6.2 Hz, 2H), 3.79 (s, 3H), 2.60-2.48 (m, 6H), 2.12-2.04 (m, 2H), 1.67-1.61 (m, 4H), 1.54-1.46 (m, 2H);

M is —C(=O)$R^M$; $R^M$ is cyclohexyl; $A^3$ is oxygen; $L^3$ is n-propyl; $Q^3$ is 1-piperidyl; and $Q^1$ is methyl; also known as, Cyclohexyl-[3-methyl-2-(3-piperidin-1-yl-propoxy)-3H-imidazol-4-yl]-methanone; M calc=333; M+H found=334;

M is —C(=O)$R^M$; $R^M$ is 4-biphenyl; $A^3$ is oxygen; $L^3$ is n-propyl; $Q^3$ is 1-piperidyl; and $Q^1$ is methyl; also known as, Biphenyl-4-yl-[3-methyl-2-(3-piperidin-1-yl-propoxy)-3H-imidazol-4-yl]-methanone; M calc=403; M+H found=404; $^1$H NMR (400 MHz, $CD_3OD$): δ 7.90-7.86 (m, 2H), 7.80-7.77 (m, 2H), 7.72-7.70 (m, 2H), 7.53-7.47 (m, 2H), 7.42-7.38 (m, 1H), 7.31 (s, 1H), 4.50 (t, J=6.2 Hz, 2H), 3.77 (s, 3H), 2.59-2.48 (m, 6H), 2.11-2.05 (m, 2H), 1.67-1.61 (m, 4H), 1.54-1.48 (m, 2H);

M is —C(=O)$R^M$; $R^M$ is hydrogen; $A^3$ is oxygen; $L^3$ is n-propyl; $Q^3$ is 1-piperidyl; and $Q^1$ is methyl; also known as, 3-Methyl-2-(3-piperidin-1-yl-propoxy)-3H-imidazol-4-yl-carbaldehyde; M calc=251; M+H found=252;

M is —CHOH$R^M$; $A^M$ is hydroxy; $R^M$ is 3,5-dichlorophenyl; $A^3$ is oxygen; $L^3$ is methyl; $Q^3$ is 4-(1-isopropylpiperidyl); and $Q^1$ is methyl; also known as, (3,5-Dichlorophenyl)-[2-(1-isopropyl-piperidin-4-ylmethoxy)-3-methyl-3H-imidazol-4-yl]-methanol; M calc=411; M+H found=412;

M is —CHOH$R^M$; $A^M$ is hydroxy; $R^M$ is 4-cyanophenyl; $A^3$ is oxygen; $L^3$ is methyl; $Q^3$ is 4-(1-isopropylpiperidyl); and $Q^1$ is methyl; also known as, 4-{Hydroxy-[2-(1-isopropyl-piperidin-4-ylmethoxy)-3-methyl-3H-imidazol-4-yl]-methyl}-benzonitrile; $^1$H NMR (400 MHz, $CDCl_3$): δ 7.57 (d), 7.48 (d), 6.20 (s), 5.72 (s), 3.13 (s), 0.96 (d);

M is —C(=O)$R^M$; $R^M$ is 3,5-dichlorophenyl; $A^3$ is oxygen; $L^3$ is methyl; $Q^3$ is 4-(1-isopropylpiperidyl); and $Q^1$ is methyl; also known as, (3,5-Dichlorophenyl)-[2-(1-isopropyl-piperidin-4-ylmethoxy)-3-methyl-3H-imidazol-4-yl]-methanone; M calc=409; M+H found=410; $^1$H NMR (400 MHz, $CDCl_3$): δ 7.65 (d, J=1.9 Hz, 2H), 7.54 (t, J=1.9 Hz, 1H), 7.25 (s, 1H), 4.33 (d, J=6.2 Hz, 2H), 3.76 (s, 3H), 3.00-2.85 (m, 2H), 2.80-2.69 (m, 1H), 2.22-2.21 (m, 2H), 1.92-1.83 (m, 2H), 1.49-1.39 (m, 2H), 1.07 (d, J=6.6 Hz, 6H).

M is —C(=O)$R^M$; $R^M$ is 2-chlorophenyl; $A^3$ is oxygen; $L^3$ is methyl; $Q^3$ is 4-(1-isopropylpiperidyl); and $Q^1$ is methyl; also known as, (2-Chlorophenyl)-[2-(1-isopropyl-piperidin-4-ylmethoxy)-3-methyl-3H-imidazol-4-yl]-methanone; M calc=375; M+H found=376; $^1$H NMR (400 MHz, $CDCl_3$): □ 7.40-7.29 (m, 2H), 7.28-7.22 (m, 2H), 6.89 (s, 1H), 4.24 (d, J=6.2 Hz, 2H), 3.75 (s, 3H), 2.91 (br d, J=11.3 Hz, 2H), 2.75-2.70 (m, 1H), 2.24-2.09 (m, 2H), 1.78 (br d, J=10.9 Hz, 2H), 1.47-1.38 (m, 2H), 1.03 (d, J=7.6 Hz, 6H);

M is —C(=O)$R^M$; $R^M$ is 4-cyanophenyl; $A^3$ is oxygen; $L^3$ is methyl; $Q^3$ is 4-(1-isopropylpiperidyl); and $Q^1$ is methyl; also known as, 4-[2-(1-Isopropyl-piperidin-4-ylmethoxy)-3-methyl-3H-imidazole-4-carbonyl]-benzonitrile; M calc=366; M+H found=367; $^1$H NMR (400 MHz, $CDCl_3$): δ 7.81-7.75 (dm, J=8.2 Hz, 2H), 7.72-7.68 (dm, J=11.1 Hz, 2H), 7.12 (s, 1H), 4.25 (d, J=6.2 Hz, 2H), 3.70 (s, 3H), 2.87 (d, J=11.4 Hz, 2H), 2.73-2.60 (m, 1H), 2.11 (t, J=11.7 Hz, 2H), 1.85-1.72 (m, 3H), 1.44-1.27 (m, 2H), 0.98 (d, J=8.8 Hz, 6H);

M is —C(=O)$R^M$; $R^M$ is 3-chlorophenyl; $A^3$ is oxygen; $L^3$ is methyl; $Q^3$ is 4-(1-isopropylpiperidyl); and $Q^1$ is methyl; also known as, (3-Chlorophenyl)-[2-(1-isopropyl-piperidin-4-ylmethoxy)-3-methyl-3H-imidazol-4-yl]-methanone; M calc=375; M+H found=376; $^1$H NMR (400 MHz, $CDCl_3$): δ 7.69 (t, J=1.7 Hz, 1H), 7.61-7.51 (dm, J=7.6 Hz, 1H), 7.48-7.44 (m, 1H), 7.34 (t, J=7.9 Hz, 1H), 7.16 (s, 1H), 4.25 (d, J=6.2 Hz, 2H), 3.69 (s, 3H), 2.94-2.83 (m, 2H), 2.74-2.64 (m, 1H), 2.18-2.07 (m, 1H), 1.84-1.72 (m, 2H), 1.70-1.32 (m, 4H), 1.00 (d, J=6.5 Hz, 6H);

M is —C(=O)$R^M$; $R^M$ is 4-trifluoromethylphenyl; $A^3$ is oxygen; $L^3$ is methyl; $Q^3$ is 4-(1-isopropylpiperidyl); and $Q^1$ is methyl; also known as, [2-(1-Isopropyl-piperidin-4-ylmethoxy)-3-methyl-3H-imidazol-4-yl]-(4-trifluoromethylphenyl)-methanone; M calc=409; M+H found=410; $^1$H NMR (400 MHz, $CDCl_3$): δ 7.83-7.77 (dm, J=8.0 Hz, 2H), 7.74 (d, J=7.6 Hz, 2H), 7.22 (s, 1H), 4.33 (d, J=6.3 Hz, H), 3.72 (s, 3H), 2.98-2.82 (m, 2H), 2.85-2.66 (m, 1H), 2.25-2.14 (m, 2H), 1.90-1.73 (m, 2H), 1.56-1.41 (m, 2H), 1.07 (d, J=6.6 Hz, 6H);

M is —C(=O)$R^M$; $R^M$ is 4-nitrophenyl; $A^3$ is oxygen; $L^3$ is methyl; $Q^3$ is 4-(1-isopropylpiperidyl); and $Q^1$ is methyl; also known as, [2-(1-Isopropyl-piperidin-4-ylmethoxy)-3-methyl-3H-imidazol-4-yl]-(4-nitro-phenyl)-methanone; M calc=386; M+H found=387; $^1$H NMR (400 MHz, CDCl$_3$): δ 8.27-8.23 (dm, J=8.7 Hz, 2H), 7.88-7.81 (dm, J=8.7 Hz, 2H), 7.14 (s, 1H), 4.26 (d, J=6.2 Hz, 2H), 3.72 (s, 3H), 2.91-2.81 (d, J=11.5 Hz, 2H), 2.15-2.05 (m, 2H), 1.84-1.72 (m, 3H), 1.43-1.27 (m, 2H), 0.99 (d, J=6.6 Hz, 6H);

M is —C(=O)$R^M$; $R^M$ is 4-fluorophenyl; $A^3$ is oxygen; $L^3$ is methyl; $Q^3$ is 4-(1-isopropylpiperidyl); and $Q^1$ is methyl; also known as, (4-Fluorophenyl)-[2-(1-isopropyl-piperidin-4-ylmethoxy)-3-methyl-3H-imidazol-4-yl]-methanone; M calc=359; M+H found=360; $^1$H NMR (400 MHz, CDCl$_3$): δ 7.78-7.69 (m, 2H), 7.12 (s, 1H), 7.11-7.03 (m, 2H), 4.24 (d, J=6.6 Hz, 2H), 3.69 (s, 3H), 2.93-2.82 (m, 2H), 2.74-2.61 (m, 1H), 2.11 (t, J=11.4 Hz, 2H), 1.77 (d, J=12.6 Hz, 2H), 1.46-1.29 (m, 2H), 1.23-1.12 (m, 1H), 0.99 (d, J=6.4 Hz, 6H); and M is —C(=O)$R^M$; $R^M$ is 4-isopropylphenyl; $A^3$ is oxygen; $L^3$ is methyl; $Q^3$ is 4-(1-isopropylpiperidyl); and $Q^1$ is methyl; also known as, (4-Isopropylphenyl)-[2-(1-isopropyl-piperidin-4-yl methoxy)-3-methyl-3H-imidazol-4-yl]-methanone; M calc=383; M+H found=384; $^1$H NMR (400 MHz, CDCl$_3$): δ 7.70-7.55 (m, 2H), 7.27-7.22 (m, 2H), 7.17 (s, 1H), 4.28-4.15 (m, 2H), 3.69 (s, 3H), 2.98-2.82 (m, 2H), 2.81-2.65 (m, 1H), 2.25-2.05 (m, 3H), 1.85-1.25 (m, 5H), 1.23-1.10 (m, 6H), 1.03 (dm J=6.2 Hz, 6H).

Example XIII

Preparation of

{3-[5-(4-Chlorobenzyl)-1-methyl-1H-imidazol-2-ylsulfanyl]-propyl}-dimethyl-amine

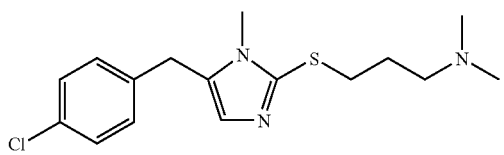

This example teaches the preparation of a compound of Formula I following Scheme VII, wherein M is —CH$_2$R$^M$; $R^M$ is p-chlorophenyl; $A^3$ is sulfur; $L^3$ is n-propyl; $Q^3$ is dimethylamino; and $Q^1$ is methyl.

The product from Example II, Step C, (0.04 g) in n-butanol (1 mL) was treated with potassium t-butoxide (0.03 g), followed by hydrazine (0.011 mL). After heating to 120° C. for 16 h, the mixture was cooled to room temperature and partitioned between brine (75 mL) and ethyl acetate (100 mL). The layers were separated and the organic portion was washed with brine (100 mL), dried over sodium sulfate, and concentrated to give the crude product. The crude material was purified by silica gel chromatography (1-5% Methanol/Dichloromethane to provide the title compound (0.017 g, 45%). M calc=323; M+H found 324. $^1$H NMR (400 MHz, CDCl$_3$): δ 7.19 (d, J=8.3 Hz, 2H), 7.01 (d, J=8.3 Hz, 2H), 6.78 (s, 1H), 3.81 (s, 2H), 3.29 (s, 3H), 2.98 (t, J=7.3 Hz, 2H), 2.29 (t, J=7.0 Hz, 2H), 2.12 (s, 6H), 1.74 (m, 2H). The compound demonstrated useful biological activity when assessed with a [$^3$H]-N-methylhistamine binding assay (see Table in Example XVIII).

Example XIV

Preparation of (4-Chlorophenyl)-[2-(3-dimethylamino-propylsulfanyl)-3-methyl-3H-imidazol-4-yl]-methanone oxime

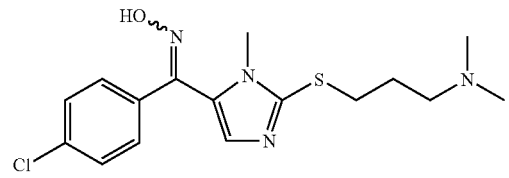

This example teaches the preparation of a compound of Formula I following Scheme VII, wherein M is —C(=N—OH)$R^M$; $R^M$ is p-chlorophenyl; $A^3$ is sulfur; $L^3$ is n-propyl; $Q^3$ is dimethylamino; and $Q^1$ is methyl.

The product from Example II, Step C (0.07 g) in ethanol (2 mL) was treated with hydroxylamine hydrochloride (0.07 g) followed by pyridine (0.08 mL). After stirring for 16 h at 80° C., the solvent was removed under reduced pressure. The residue was then partitioned between water (75 mL) and ethyl acetate (100 mL). The layers were separated and the organic portion was washed with brine (100 mL). The aqueous portion was treated with solid sodium bicarbonate until the solution reached pH=7. The aqueous portion was extracted with ethyl acetate (4×50 mL) and dichloromethane (2×50 mL). The combined organic extracts were dried over sodium sulfate, and concentrated to provide the crude product. The crude material was purified by silica gel chromatography (1-5% Methanol (2 M NH$_3$)/dichloromethane to provide the title compound as a mixture of oxime isomers (0.01 g, 14%), M calc=352, M+H found=353; $^1$H NMR (400 MHz, CDCl$_3$): δ 7.43-7.37 (m, 1.4H), 7.32-7.28 (m, 1.3H), 7.25-7.20 (m, 1.3H), 6.99 (s, 0.6H), 6.62 (s, 0.4H), 3.66 (s, 1H), 3.26 (s, 2H), 3.12-3.04 (m, 2H), 2.47-2.36 (m, 2H), 2.23 (s, 6H), 1.94-1.82 (m, 2H). The compound demonstrated useful biological activity when assessed with a [$^3$H]-N-methylhistamine binding assay (see Table in Example XVIII).

Example XV

Preparation of

[3-Methyl-2-(3-piperidin-1-yl-propoxy)-3H-imidazol-4-yl]-piperidin-1-yl-methane

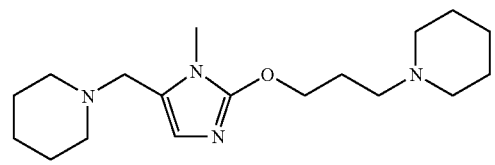

This example teaches the preparation of a compound of Formula I following Scheme XII, wherein M is —CH$_2$R$^M$;

$R^M$ is 1-piperidyl; $A^3$ is oxygen; $L^3$ is n-propyl; $Q^3$ is 1-piperidyl; and $Q^1$ is methyl.

To a stirred solution of 3-methyl-2-(3-piperidin-1-yl-propoxy)-3H-imidazole-4-carbaldehyde (10.0 mg) and piperidine (3.41 mg) in 1,2-dichloroethane was added at room temperature sodium triacetoxyborohydride (12.7 mg). The reaction mixture was stirred for 18 h at room temperature and dichloromethane (5.00 mL) and saturated sodium bicarbonate (2.00 mL) were added. The mixture was stirred for 1 h at room temperature and additional dichloromethane (100 mL) was added. The organic layer was washed with saturated sodium bicarbonate (20.0 mL) and water (2×20.0 mL) and was dried over magnesium sulfate. The solvent was removed in vacuo and the residue was purified by flash chromatography on silica gel (CHCl$_3$/NH$_3$, 2 M in methanol) to give the title compound (1.00 mg). M calc=320; M+H found=321. $^1$H NMR (400 MHz, CD$_3$OD): δ 6.42 (s, 1H), 4.30 (t, J=6.2 Hz, 2H), 3.40 (s, 3H), 3.34 (s, 2H), 2.57-2.38 (m, 10H), 2.04-1.96 (m, 2H), 1.67-1.41 (m, 12H). The compound demonstrated useful biological activity when assessed with a [$^3$H]-N-methylhistamine binding assay (see Table in Example XVIII).

Example XVI

Preparation of (4-Chloro-phenyl)-[2-(3-dimethylamino-propane-1-sulfinyl)-3-methyl-3H-imidazol-4-yl]-methanone

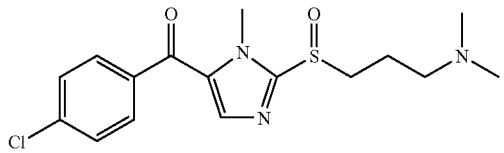

This example teaches the preparation of a compound of Formula I following Scheme XI, wherein M is —C(=O)$R^M$; $R^M$ is p-chlorophenyl; $A^3$ is S(O); $L^3$ is n-propyl; $Q^3$ is dimethylamino; and $Q^1$ is methyl.

Step A: Preparation of (4-Chloro-phenyl)-[2-(3-dimethylamino-propane-1-sulfinyl)-3-methyl-3H-imidazol-4-yl]-methanone To a stirred solution of (4-Chloro-phenyl)-[2-(3-dimethylamino-propylsulfanyl)-3-methyl-3H-imidazol-4-yl]-methanone (135 mg) in glacial acetic acid (4.00 mL) was added at room temperature H$_2$O$_2$ (82.0 μL; 30 wt. % in water). The reaction solution was stirred for 48 h at room temperature, and water (10.0 mL) was added. The solution was brought to pH=12 using sodium hydroxide (25% in water) and extracted with dichloromethane (250 mL, 2×50.0 mL). The combined organic layers were washed with water (3×20.0 mL) and were dried over magnesium sulfate. The solvent was removed in vacuo, and the residue was purified by flash chromatography on silica gel (CHCl$_3$/NH$_3$, 2 M in methanol) to give the title compound (121 mg). M calc=353; M+H found=354. $^1$H NMR (400 MHz, CD$_3$OD): δ 7.91-7.87 (m, 2H), 7.70 (s, 1H), 7.60-7.55 (m, 2H), 4.21 (s, 3H), 3.61-3.48 (m, 2H), 2.54-2.43 (m, 2H), 2.21 (s, 6H), 2.04-1.94 (m, 2H). The compound demonstrated useful biological activity when assessed with a [$^3$H]-N-methylhistamine binding assay (see Table in Example XVI II).

Step B: Additional Compounds Prepared Following Scheme XI, and Example XVI, Step A.

The following compounds of Formula I were prepared following Scheme XI and Example XVI, Step A; and substituting reagents, and adjusting reaction conditions as needed.

The compounds of Formula I, wherein:

M is —C(=O)$R^M$; $R^M$ is p-chlorophenyl; $A^3$ is S(O$_2$); $L^3$ is n-propyl; $Q^3$ is dimethylamino; and $Q^1$ is methyl; also known as, (4-Chlorophenyl)-[2-(3-dimethylamino-propane-1-sulfonyl)-3-methyl-3H-imidazol-4-yl]-methanone; M calc=369; M+H found=370; K$_i$=10000; and M is —C(=O)$R^M$; $R^M$ is p-chlorophenyl; $A^3$ is S(O$_2$); $L^3$ is n-propyl; $Q^3$ is dimethylazinoyl; and $Q^1$ is methyl; also known as, (4-Chlorophenyl)-[2-(3-dimethylamino-propane-1-sulfonyl)-3-methyl-3H-imidazol-4-yl]-methanone oxide; M calc=385; M+H found=386; K$_i$=10000.

Example XVIII

In Vitro

Transfection of Cells with Human Histamine Receptor

A 10 cm tissue culture dish with a confluent monolayer of SK-N-MC cells was split two days prior to transfection. Using sterile technique the media was removed and the cells were detached from the dish by the addition of trypsin. One fifth of the cells were then placed onto a new 10 cm dish. Cells were grown in a 37° C. incubator with 5% CO$_2$ in Minimal Essential Media Eagle with 10% Fetal Bovine Serum. After two days cells were approximately 80% confluent. These were removed from the dish with trypsin and pelleted in a clinical centrifuge. The pellet was then re-suspended in 400 μL complete media and transferred to an electroporation cuvette with a 0.4 cm gap between the electrodes (Bio-Rad #165-2088). One μg supercoiled H$_3$ receptor cDNA was added to the cells and mixed. The voltage for the electroporation was set at 0.25 kV, the capacitance is set at 960 μF. After electroporation the cells were diluted into 10 mL complete media and plated onto four 10 cm dishes. Because of the variability in the efficiency of electroporation four different concentrations of cells were plated. The ratios used were; 1:20, 1:10, 1:5, with the remainder of the cells being added to the fourth dish. The cells were allowed to recover for 24 h before adding the selection media (complete media with 600 μg/mL G418). After 10 days dishes were analyzed for surviving colonies of cells. Dishes with well isolated colonies were used. Cells from individual colonies were isolated and tested. SK-N-MC cells were used because they give efficient coupling for inhibition of adenylate cyclase. The clones that gave the most robust inhibition of adenylate cyclase in response to histamine were used for further study.

[3H]-N-methylhistamine Binding

Cell pellets from histamine H$_3$ receptor-expressing SK-N-MC cells were homogenized in 20 mM Tris HCl/0.5 mM EDTA. Supernatants from a 800 g spin were collected, recentrifuged at 30,000 g for 30 minutes. Pellets were re-homogenized in 50 mM Tris/5 mM EDTA (pH 7.4). Membranes were incubated with 0.8 nM [$^3$H]-N-methylhistamine plus/minus test compounds for 45 min at 25° C. and harvested by rapid filtration over GF/C glass fiber filters (pretreated with 0.3% polyethylenimine) followed by four washes with ice cold buffer. Filters were dried, added to 4 mL scintillation cocktail and then counted on a liquid scintillation counter. Non-specific binding was defined with 10 μM histamine. $PK_i$ values were calculated based on a $K_D$ of 800 pM and a ligand concentration ([L]) of 800 pM according to the formula:

$$K_i=(IC_{50})/(1+([L]/(K_D)))$$

$K_i$ Values

| Example | Compound Name | $K_i$ (nM) |
|---|---|---|
| I | (4-Chloro-phenyl)-[2-(2-dimethylamino-ethyl-sulfanyl)-3-methyl-3H-imidazol-4-yl]-methanone | 98 |
| II | (4-Chlorophenyl)-[2-(3-dimethylamino-propylsulfanyl)-3-methyl-3H-imidazol-4-yl]-methanone | 2 |
| II | (4-Chlorophenyl)-[3-methyl-2-(3-piperidin-1-yl-propylsulfanyl)-3H-imidazol-4-yl]-methanone | 3.1 |
| III | (4-Bromophenyl)-[3-methyl-2-(3-piperidin-1-yl-propylsulfanyl)-3H-imidazol-4-yl]-methanone | 7.5 |
| III | (4-Bromophenyl)-[2-(3-dimethylamino-propylsulfanyl)-3-methyl-3H-imidazol-4-yl]-methanone | 1.6 |
| IV | (4-Chlorophenyl)-{3-methyl-2-[2-(1-methylpyrrolidin-2-yl)-ethylsulfanyl]-3H-imidazol-4-yl}-methanone | 2 |
| IV | [2-(3-Dimethylamino-propylsulfanyl)-3-methyl-3H-imidazol-4-yl]-phenyl-methanone | 4 |
| IV | (4-Chlorophenyl)-[3-methyl-2-(1-methyl-piperidin-4-ylsulfanyl)-3H-imidazol-4-yl]-methanone | 7 |
| V | (4-Chloro-phenyl)-[2-(1-isopropyl-piperidin-4-ylmethoxy)-3-methyl-3H-imidazol-4-yl]-methanone | 3.7 |
| V | (4-Chlorophenyl)-[3-methyl-2-(3-piperidin-1-yl-propylamino)-3H-imidazol-4-yl]-methanone | 32 |
| V | (4-Bromophenyl)-[2-(1-isopropyl-piperidin-4-ylmethoxy)-3-methyl-3H-imidazol-4-yl]-methanone | 5.3 |
| V | (4-Bromophenyl)-[2-(1-ethyl-piperidin-4-ylmethoxy)-3-methyl-3H-imidazol-4-yl]-methanone | 6.6 |
| V | (4-Bromophenyl)-[2-(1-sec-butyl-piperidin-4-ylmethoxy)-3-methyl-3H-imidazol-4-yl]-methanone | 9 |
| XI | (4-Chlorophenyl)-[2-(1-isopropyl-piperidin-4-yloxy)-3-methyl-3H-imidazol-4-yl]-methanone | 25 |
| XI | (4-Chlorophenyl)-[2-(1-isopropyl-piperidin-4-ylsulfanyl)-3-methyl-3H-imidazol-4-yl]-methanone | 3 |
| XII | [3-Methyl-2-(3-piperidin-1-yl-propoxy)-3H-imidazol-4-yl]-naphthalen-1-yl-methanone | 79 |
| XII | (2-Chlorophenyl)-[2-(1-isopropyl-piperidin-4-ylmethoxy)-3-methyl-3H-imidazol-4-yl]-methanone | 1.3 |
| XII | (4-Fluorophenyl)-[2-(1-isopropyl-piperidin-4-ylmethoxy)-3-methyl-3H-imidazol-4-yl]-methanone | 2.5 |
| XII | (3-Chlorophenyl)-[2-(1-isopropyl-piperidin-4-ylmethoxy)-3-methyl-3H-imidazol-4-yl]-methanone | 2.8 |
| XII | (3,5-Dichlorophenyl)-[2-(1-isopropyl-piperidin-4-ylmethoxy)-3-methyl-3H-imidazol-4-yl]-methanone | 4 |
| XII | [2-(1-Isopropyl-piperidin-4-ylmethoxy)-3-methyl-3H-imidazol-4-yl]-(4-trifluoromethyl-phenyl)-methanone | 4.1 |
| XII | [2-(1-Isopropyl-piperidin-4-ylmethoxy)-3-methyl-3H-imidazol-4-yl]-(4-nitro-phenyl)-methanone | 4.6 |
| XII | 4-{Hydroxy-[2-(1-isopropyl-piperidin-4-ylmethoxy)-3-methyl-3H-imidazol-4-yl]-methyl}-benzonitrile | 7.6 |
| XIII | {3-[5-(4-Chlorobenzyl)-1-methyl-1H-imidazol-2-ylsulfanyl]-propyl}-dimethyl-amine | 22 |
| XIV | (4-Chlorophenyl)-[2-(3-dimethylamino-propylsulfanyl)-3-methyl-3H-imidazol-4-yl]-methanone oxime | 3.2 |
| XV | [3-Methyl-2-(3-piperidin-1-yl-propoxy)-3H-imidazol-4-yl]-piperidin-1-yl-methane | 36.4 |
| XVI | (4-Chlorophenyl)-[2-(3-dimethylamino-propane-1-sulfinyl)-3-methyl-3H-imidazol-4-yl]-methanone | 315 |

What is claimed is:

1. A compound selected from the group consisting of:
(2-Chlorophenyl)-[2-(1-isopropyl-piperidin-4-yl-methoxy)-3-methyl-3H-imidazol-4-yl]-methanone;
(4-Bromophenyl)-[2-(3-dimethylamino-propylsulfanyl)-3-methyl-3H-imidazol-4-yl]-methanone;
(4-Chlorophenyl)-{3-methyl-2-[2-(1-methylpyrrolidin-2-yl)-ethylsulfanyl]-3H-imidazol-4-yl}-methanone;
(4-Fluorophenyl)-[2-(1-isopropyl-piperidin-4-yl-methoxy)-3-methyl-3H-imidazol-4-yl]-methanone;
(3-Chlorophenyl)-[2-(1-isopropyl-piperidin-4-yl-methoxy)-3-methyl-3H-imidazol-4-yl]-methanone;
(4-Chlorophenyl)-[2-(1-isopropyl-piperidin-4-ylsulfanyl)-3-methyl-3H-imidazol-4-yl]-methanone;
(4-Chlorophenyl)-[3-methyl-2-(3-piperidin-1-yl-propylsulfanyl)-3H-imidazol-4-yl]-methanone;
(4-Chlorophenyl)-[2-(3-dimethylamino-propylsulfanyl)-3-methyl-3H-imidazol-4-yl]-methanone oxime;
(4-Chlorophenyl)-[2-(1-isopropyl-piperidin-4-yl-methoxy)-3-methyl-3H-imidazol-4-yl]-methanone;
[2-(3-Dimethylamino-propylsulfanyl)-3-methyl-3H-imidazol-4-yl]-phenyl-methanone;
(3,5-Dichlorophenyl)-[2-(1-isopropyl-piperidin-4-yl-methoxy)-3-methyl-3H-imidazol-4-yl]-methanone;
[2-(1-Isopropyl-piperidin-4-ylmethoxy)-3-methyl-3H-imidazol-4-yl]-(4-trifluoromethyl-phenyl)-methanone;
[2-(1-Isopropyl-piperidin-4-ylmethoxy)-3-methyl-3H-imidazol-4-yl]-(4-nitro-phenyl)-methanone;
(4-Bromophenyl)-[2-(1-isopropyl-piperidin-4-yl-methoxy)-3-methyl-3H-imidazol-4-yl]-methanone;
(4-Bromophenyl)-[2-(1-ethyl-piperidin-4-ylmethoxy)-3-methyl-3H-imidazol-4-yl]-methanone;
(4-Chlorophenyl)-[3-methyl-2-(1-methyl-piperidin-4-yl-sulfanyl)-3H-imidazol-4-yl]-methanone;
(4-Bromophenyl)-[3-methyl-2-(3-piperidin-1-yl-propyl-sulfanyl)-3H-imidazol-4-yl methanone;
4-{Hydroxy-[2-(1-isopropyl-piperidin-4-ylmethoxy)-3-methyl-3H-imidazol-4-yl]-methyl}-benzonitrile; and
(4-Bromophenyl)-[2-(1-sec-butyl-piperidin-4-yl-methoxy)-3-methyl-3H-imidazol-4-yl]-methanone;
or a pharmaceutically acceptable salt thereof.

2. A compound of claim 1, selected from the group consisting of:
(2-Chlorophenyl)-[2-(1-isopropyl-piperidin-4-yl-methoxy)-3-methyl-3H-imidazol-4-yl]-methanone;
(4-Bromophenyl)-[2-(3-dimethylamino-propylsulfanyl)-3-methyl-3H-imidazol-4-yl]-methanone;
(4-Chlorophenyl)-{3-methyl-2-[2-(1-methylpyrrolidin-2-yl)-ethylsulfanyl]-3H-imidazol-4-yl}-methanone;
(4-Fluorophenyl)-[2-(1-isopropyl-piperidin-4-yl-methoxy)-3-methyl-3H-imidazol-4-yl]-methanone;
(3-Chlorophenyl)-[2-(1-isopropyl-piperidin-4-yl-methoxy)-3-methyl-3H-imidazol-4-yl]-methanone;
(4-Chlorophenyl)-[2-(1-isopropyl-piperidin-4-ylsulfanyl)-3-methyl-3H-imidazol-4-yl]-methanone;
(4-Chlorophenyl)-[3-methyl-2-(3-piperidin-1-yl-propyl-sulfanyl)-3H-imidazol-4-yl]-methanone;
(4-Chlorophenyl)-[2-(3-dimethylamino-propylsulfanyl)-3-methyl-3H-imidazol-4-yl]-methanone oxime;
(4-Chlorophenyl)-[2-(1-isopropyl-piperidin-4-yl-methoxy)-3-methyl-3H-imidazol-4-yl]-methanone;
[2-(3-Dimethylamino-propylsulfanyl)-3-methyl-3H-imidazol-4-yl]-phenyl-methanone;
(3,5-Dichlorophenyl)-[2-(1-isopropyl-piperidin-4-yl-methoxy)-3-methyl-3H-imidazol-4-yl]-methanone;
[2-(1-Isopropyl-piperidin-4-ylmethoxy)-3-methyl-3H-imidazol-4-yl]-(4-trifluoromethyl-phenyl)-methanone;
[2-(1-Isopropyl-piperidin-4-ylmethoxy)-3-methyl-3H-imidazol-4-yl]-(4-nitro-phenyl)-methanone; and (4-Bromophenyl)-[2-(1-isopropyl-piperidin-4-yl-methoxy)-3-methyl-3H-imidazol-4-yl]-methanone;
or a pharmaceutically acceptable salt thereof.

3. A compound of claim 2 selected from the group consisting of:
(4-Fluorophenyl)-[2-(1-isopropyl-piperidin-4-yl-methoxy)-3-methyl-3H-imidazol-4-yl]-methanone;
(4-Chlorophenyl)-[2-(1-isopropyl-piperidin-4-yl-methoxy)-3-methyl-3H-imidazol-4-yl]-methanone; and
[2-(1-Isopropyl-piperidin-4-ylmethoxy)-3-methyl-3H-imidazol-4-yl]-(4-nitro-phenyl)-methanone;
or a pharmaceutically acceptable salt thereof.

4. The compound of claim 3 having the formula (4-Chlorophenyl)-[2-(1-isopropyl-piperidin-4-ylmethoxy)-3-methyl-3H-imidazol-4-yl]-methanone or a pharmaceutically acceptable salt thereof.

5. The compound of claim 3 having the formula (4-Fluorophenyl)-[2-(1-isopropyl-piperidin-4-ylmethoxy)-3-methyl-3H-imidazol-4-yl]-methanone or a pharmaceutically acceptable salt thereof.

6. The compound of claim 3 having the formula [2-(1-Isopropyl-piperidin-4-ylmethoxy)-3-methyl-3H-imidazol-4-yl]-(4-nitro-phenyl)-methanone or a pharmaceutically acceptable salt thereof.

7. A pharmaceutical composition comprising a pharmaceutically acceptable excipient and a compound of claim 1.

8. A method of treating a subject having a disease or condition modulated by histamine $H_3$ receptor activity, comprising administering to the subject a therapeutically effective amount of a compound of claim 1, wherein said disease or condition is selected from the group consisting of sleep/wake disorders, arousal/vigilance disorders, migraine, epilepsy and narcolepsy.

9. A process for the production of a compound of the formula (11):

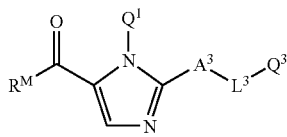

(11)

wherein:
$Q^1$ is selected from the group consisting of $C_{1-7}$ alkyl, $C_{1-7}$ haloalkyl and $C_{2-7}$ alkenyl;
wherein $Q^1$ may be substituted with one or more substituents selected from the group consisting of halo, cyano, hydroxy, $OR^{11}$, $C_{1-5}$ alkyl, $C_{1-5}$ haloalkyl, $C_{2-5}$ alkenyl, nitro, amino ($H_2N$—), $R^{11}HN$—, $R^{11}R^{12}N$—, ($H_2NC(O)$), $R^{11}HNC(O)$, $R^{11}R^{12}NC(O)$ and $R^{11}OC(O)$, and
wherein $R^{11}$ and $R^{12}$ are independently $C_{1-5}$ alkyl, $C_{1-5}$ haloalkyl or $C_{2-5}$ alkenyl;
$R^M$ is selected from the group consisting of $C_{1-7}$ alkyl, $R^{M1}HN$—$R^{M1}R^{M2}N$—, $C_{3-7}$ cycloalkyl, aryl, biaryl and 4-7 membered heterocyclyl,
wherein $R^M$ may be substituted with one or more substituents independently selected from the group consisting of halo, cyano, hydroxy, $OR^{M1}$, $C_{1-5}$ alkyl, $C_{1-5}$ haloalkyl, $C_{2-5}$ alkenyl, nitro, amino ($H_2N$—), $R^{M1}HN$—, $R^{M1}R^{M2}N$—, amido($H_2NC(O)$), $R^{M1}HNC(O)$ and $R^{M1}R^{M2}NC(O)$, and
wherein $R^{M1}$ and $R^{M2}$ are independently $C_{1-5}$ alkyl, $C_{1-5}$ haloalkyl or $C_{2-5}$ alkenyl;

$A^3$ is NH, $NR^3$, sulfur or oxygen, wherein $R^3$ is $C_{1-5}$ alkyl;
$L^3$ is $C_{1-7}$ alkyl or $C_{2-7}$ alkenyl;
wherein $L^3$ may be substituted with one or more substituents selected from the group consisting of halo, hydroxy, methoxy and amino ($H_2N$—);
or $L^3$ is absent; and
$Q^3$ is selected from the group consisting of $C_{1-7}$ alkyl, $C_{1-7}$ haloalkyl, $C_{2-7}$ alkenyl, $C_{3-7}$ cycloalkyl, $C_{5-7}$ cycloalkenyl, aryl, 4-7 membered heterocyclyl, $C_{3-7}$ cycloalkyl-4-7 membered heterocyclyl, 4-7 membered heterocyclyl-$C_{3-7}$ cycloalkyl, bi-(4-7 membered heterocyclyl), $R^{31}HN$—, $R^{31}R^{32}N$—, azinoyl($R^{31}HN^+(O^-)$ or $R^{31}R^{32}N^+(O^-)$), $C_{3-7}$ cycloalkylamino, 4-7 membered heterocyclylamino, aryl $C_{1-6}$ alkylamino, $C_{3-7}$ cycloalkylsulfanyl, 4-7 membered heterocyclylsulfanyl and 4-7 membered heterocyclyloxy;
wherein $Q^3$ may be substituted with one or more substituents selected from the group consisting of halo, cyano, hydroxy, $OR^{31}$, $C_{1-5}$ alkyl, $C_{1-5}$ haloalkyl, $C_{2-5}$ alkenyl, nitro, amino($H_2N$—), $R^{31}HN$—, $R^{31}R^{32}N$—, ($H_2NC(O)$), $R^{31}HNC(O)$, $R^{31}R^{32}NC(O)$, $R^{31}OC(O)$, $C_{3-7}$ cycloalkyl, monocyclic 4-7 membered heterocyclyl and monocyclic 4-7 membered heterocyclyl-$C_{1-6}$ alkyl, and
wherein $R^{31}$ and $R^{32}$ are independently $C_{1-5}$ alkyl, $C_{1-5}$ haloalkyl or $C_{2-5}$ alkenyl;
that comprises treating a compound of the formula (5b)

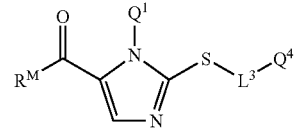

(5b)

wherein $Q^4$ is hydrogen, with an oxidizing agent resulting in an intermediate compound of the formula (10)

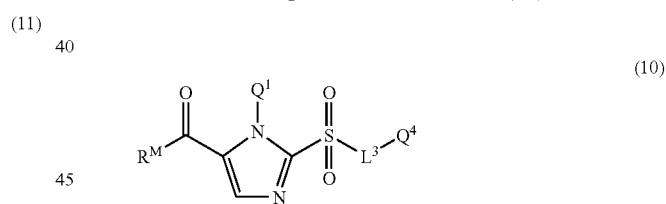

(10)

and treating said intermediate compound (10) with a reagent H—$A^3$—$L^3$—$Q^3$, wherein $L^3$ of the reagent H—$A^3$—$L^3$—$Q^3$ is independent of $L^3$ of formula (5b) and formula (10), in the presence of a base in a suitable solvent yielding said compound of formula 11.

10. A process according to claim 9, wherein said oxidizing agent is either hydrogen peroxide in acetic acid, or 3-chloroperoxybenzoic acid in dichloromethane or diethyl ether.

11. A process according to claim 9, wherein said base is an alkali metal hydride.

12. A process according to claim 11, wherein said alkali metal hydride is sodium hydride.

13. A process according to claim 9, wherein said suitable solvent is a member selected from the group consisting of dimethylformamide, benzene, 1,2-dimethoxyethane and tetrahydrofuran.

14. A process according to claim 13, wherein said suitable solvent is tetrahydrofuran.

* * * * *